United States Patent
Winkler et al.

(10) Patent No.: US 9,550,730 B2
(45) Date of Patent: Jan. 24, 2017

(54) MEROCYANINE DERIVATIVES

(75) Inventors: Barbara Winkler, Lorrach (DE); Dietmar Hueglin, Basel (CH); Kai Eichin, Kandern (DE); Larissa Ehrsam, Riehen (CH); Xavier Marat, Paris (FR); Hervé Richard, Gagny (FR); ILona Marion Kienzle, Weil am Rhein/Markt (DE); Ute Schroeder, White Plains, NY (US)

(73) Assignee: BASF SE, Ludwigshafen (DE)

( * ) Notice: Subject to any disclaimer, the term of this patent is extended or adjusted under 35 U.S.C. 154(b) by 15 days.

(21) Appl. No.: 14/232,915

(22) PCT Filed: Jul. 19, 2012

(86) PCT No.: PCT/IB2012/053688
§ 371 (c)(1),
(2), (4) Date: Jan. 15, 2014

(87) PCT Pub. No.: WO2013/011480
PCT Pub. Date: Jan. 24, 2013

(65) Prior Publication Data
US 2014/0150380 A1 Jun. 5, 2014

(30) Foreign Application Priority Data

Jul. 21, 2011 (WO) .................. PCT/EP2011/062531

(51) Int. Cl.
*C07C 255/30* (2006.01)
*C07C 255/07* (2006.01)
(Continued)

(52) U.S. Cl.
CPC ............. *C07C 255/30* (2013.01); *A01N 25/00* (2013.01); *B65B 3/00* (2013.01); *C07C 255/31* (2013.01); *C07D 295/14* (2013.01); *C07D 295/145* (2013.01); *C07D 307/42* (2013.01); *C07D 307/52* (2013.01); *C07D 317/24* (2013.01); *C07D 317/28* (2013.01); *C08K 5/315* (2013.01); *C08K 5/3435* (2013.01); *C08K 5/357* (2013.01); *C07C 2101/16* (2013.01)

(58) Field of Classification Search
CPC ..... C07C 255/30; C07C 255/07; C07C 255/00
See application file for complete search history.

(56) References Cited

U.S. PATENT DOCUMENTS

2003/0003396 A1  1/2003  Berneth et al.
2009/0169495 A1  7/2009  Wagner et al.
(Continued)

FOREIGN PATENT DOCUMENTS

CN   101346348 A     1/2009
DE   WO 02080161 A2 * 10/2002 ........... C07D 217/14
(Continued)

OTHER PUBLICATIONS

English Language Abst. of JP2011073214 Apr. 14, 2011.
International Search Report dated Dec. 27, 2012.
International Prel. Rep. on Patentability dated Jan. 21, 2014.
English Language Abst. of FR2957251 Sep. 16, 2011.

*Primary Examiner* — Nyeemah A Grazier
(74) *Attorney, Agent, or Firm* — Marshall, Gerstein & Borun LLP

(57) ABSTRACT

Disclosed are compounds of formula (1) and (2) and/or E/E-, E/Z- or Z/Z geometrical isomer forms thereof; wherein R1-R5, R1-R11 and A are defined as in description. The compounds are used as UV absorbers for protecting household products from photolytic and oxidative degradation, as plastic additives, preferably for food and pharmaceutical packaging applications, for preventing photo-degradation of food by incorporation of the compounds of formula (1') and/or (2') into transparent food containers, for protection of UV-A sensitive drugs from photo-degradation by incorporation of UV absorber in transparent blister foils or transparent pharmacy containers, as additives for photographic and printing applications, as additives for electronic applications and protecting the ingredients in agriculture applications.

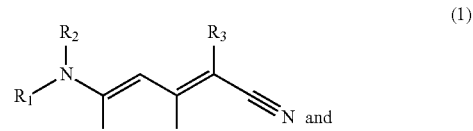

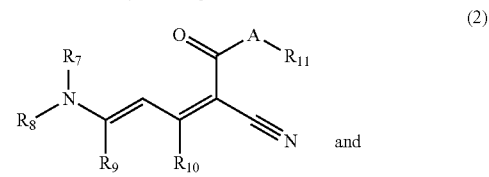

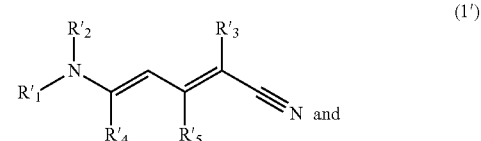

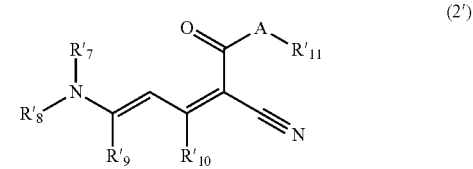

10 Claims, No Drawings

(51) Int. Cl.
*C07C 255/00* (2006.01)
*C07D 317/28* (2006.01)
*C07C 255/31* (2006.01)
*C07D 295/14* (2006.01)
*C07D 307/42* (2006.01)
*C07D 307/52* (2006.01)
*A01N 25/00* (2006.01)
*B65B 3/00* (2006.01)
*C07D 295/145* (2006.01)
*C07D 317/24* (2006.01)
*C08K 5/315* (2006.01)
*C08K 5/3435* (2006.01)
*C08K 5/357* (2006.01)

(56) References Cited

U.S. PATENT DOCUMENTS

2010/0025642 A1 2/2010 Hanaki et al.
2013/0058990 A1 3/2013 Richard et al.
2013/0064871 A1 3/2013 Richard et al.

FOREIGN PATENT DOCUMENTS

| FR | 2957251 A1 | 9/2011 |
| JP | 2009096973 A * | 5/2009 |
| JP | 2011073214 A | 4/2011 |
| WO | 02080161 A2 | 10/2002 |
| WO | 2011113718 A1 | 9/2011 |
| WO | 2011113719 A2 | 9/2011 |

* cited by examiner

MEROCYANINE DERIVATIVES

The present invention refers to novel merocyanine derivatives comprising specific polar groups consisting of hydroxyl- and ether-functionalities.

Furthermore the present invention relates to the use of these compounds for protecting household products from photolytic and oxidative degradation, as plastic additives, preferably for food and pharmaceutical packaging applications, for preventing photo-degradation of food by incorporation of these compounds into transparent food containers, for protection of UV-A sensitive drugs from photo-degradation by incorporation of UV absorber in transparent blister foils or transparent pharmacy containers, as additives for photographic and printing applications, as additives for electronic applications and for protecting the ingredients in agriculture applications.

Accordingly, the present invention relates to the compounds of formula

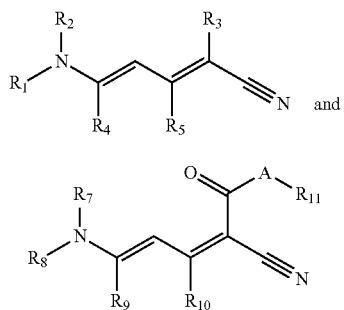

and/or its E/E-, E/Z- or Z/Z-geometrical isomer forms, wherein $R_1$ and $R_2$ independently of each other are hydrogen; $C_1$-$C_{22}$alkyl, $C_2$-$C_{22}$alkenyl, $C_2$-$C_{22}$alkinyl, which are optionally substituted by at least one hydroxy; or $R_1$ and $R_2$ together with the nitrogen atom linking them form a —(CH$_2$)$_n$— ring which is optionally interrupted by —O— or by —NH—;

$R_3$ is a —(C=O)OR$_6$ group; or a —(CO)NHR$_6$ group;

$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;

$R_4$ and $R_5$ are hydrogen; or $R_4$ and $R_5$ form a —(CH$_2$)$_n$— ring which is optionally substituted by $C_1$-$C_4$alkyl and/or interrupted by one or more than one —O— or by —NH—;

n is a number from 2 to 7;

$R_7$ and $R_8$ independently of each other are hydrogen; $C_1$-$C_{22}$alkyl, $C_2$-$C_{22}$alkenyl, $C_2$-$C_{22}$alkinyl, which is optionally interrupted by one or more than one O and/or substituted by one or more than one OH, $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—; or $R_7$ and $R_8$ together with the nitrogen atom linking them form a —(CH$_2$)$_n$— ring which is optionally interrupted by one or more than one —O—;

$R_9$ and $R_{10}$ are hydrogen; or $R_9$ and $R_{10}$ form a —(CH$_2$)$_n$— ring which is optionally substituted by $C_1$-$C_4$alkyl and/or interrupted by —O— or by —NH—;

A is —O—; or —NH;

$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O; or $C_1$-$C_{22}$alkyl or $C_2$-$C_{22}$alkenyl which is substituted by $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—;

with the proviso that (I) at least one of $R_1$, $R_2$ and $R_6$ is substituted by hydroxy;

(II) if one of $R_1$ is hydroxyethyl, $R_2$ is not hydrogen, methyl or ethyl or hydroxyethyl; and if $R_1$ is hydrogen, $R_2$ is not 1-hydroxy-3-methyl-but-2-yl;

(III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical;

(IV) at least one of $R_7$ and $R_8$, or $R_{11}$ is interrupted by one or more than one —O—.

Preferred are compounds of formula (1) or (2), wherein $R_1$ and $R_2$ independently of each other are hydrogen; $C_1$-$C_{22}$alkyl, $C_2$-$C_{22}$alkenyl, $C_2$-$C_{22}$alkinyl, which are optionally substituted by at least one hydroxy; or $R_1$ and $R_2$ together with the nitrogen atom linking them form a —(CH$_2$)$_n$— ring which is optionally interrupted by —O— or by —NH—;

$R_3$ is a —(C=O)OR$_6$ group; or a —(CO)NHR$_6$ group;

$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;

$R_4$ and $R_5$ are hydrogen; or $R_4$ and $R_5$ form a —(CH$_2$)$_n$— ring which is optionally substituted by $C_1$-$C_4$alkyl and/or interrupted by —O— or by —NH—;

n is a number from 2 to 7;

$R_7$ and $R_8$ independently of each other are hydrogen; $C_1$-$C_{22}$alkyl, $C_2$-$C_{22}$alkenyl, $C_2$-$C_{22}$alkinyl, which is optionally interrupted by one or more than one O and/or substituted by one or more than one OH; or $R_7$ and $R_8$ together with the nitrogen atom linking them form a —(CH$_2$)$_n$— ring which is optionally interrupted by one or more than one —O—;

$R_9$ and $R_{10}$ are hydrogen; or $R_9$ and $R_{10}$ form a —(CH$_2$)$_n$— ring which is optionally substituted by $C_1$-$C_4$alkyl and/or interrupted by —O— or by —NH—;

A is —O—; or —NH;

$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O;

with the proviso that (I) at least one of $R_1$, $R_2$ and $R_6$ is substituted by hydroxy;

(II) if one of $R_1$ is hydroxyethyl, $R_2$ is not hydrogen, methyl or ethyl or hydroxyethyl; and if $R_1$ is hydrogen, $R_2$ is not 1-hydroxy-3-methyl-but-2-yl;

(lll) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical;

(IV) at least one of $R_7$ and $R_8$, or $R_{11}$ is interrupted by one or more than one —O—.

Preferred are compounds of formula (1), wherein $R_1$ and $R_2$ independently of each other are hydrogen; $C_4$-$C_{12}$alkyl; or hydroxy-$C_3$-$C_{12}$alkyl;

wherein at least one of $R_1$ and $R_2$ is hydroxy-$C_3$-$C_{12}$alkyl; and $R_3$, $R_4$ and $R_5$ are defined as in claim 1.

Preferred are also compounds of formula (1), wherein $R_6$ is $C_1$-$C_{12}$alkyl, which is optionally substituted by one or more than one hydroxy.

More preferred are also compounds of formula (1), wherein $R_6$ is $C_1$-$C_{12}$alkyl which is substituted by one or more than one hydroxy;

one of $R_1$ and $R_2$ is $C_4$-$C_{22}$alkyl; or $R_1$ and $R_2$ together with the nitrogen atom linking them form a —$(CH_2)_n$-ring which is optionally interrupted by —O— and/or —NH—; and $R_4$ and $R_5$ and n are defined as in claim 1.

Preferred are compounds of formula (2), wherein $R_{11}$ is a radical of formula (1a) —$(CH_2)_m$—O—$R_{12}$, wherein $R_{12}$ is $C_1$-$C_{12}$alkyl; or $C_1$-$C_6$alkoxy-$C_1$-$C_6$alkyl;

m is a number from 1 to 5; and $R_7$, $R_8$, $R_9$, $R_{10}$ and A are defined as in claim 1.

Even more preferred are compounds of formulas (1) and (2), wherein $R_1$ and $R_2$ and $R_7$ and $R_8$ respectively together with the linking nitrogen atom form a piperidyl radical; or a morpholinyl radical.

Preferred are also compounds of formulas (1) and (2), wherein $R_4$ and $R_5$ and $R_9$ and $R_{10}$ respectively form a carbocyclic ring which contains 6 carbon atoms.

Most preferred are compounds of formula (1), wherein $R_1$ and $R_2$ independently of each other are hydrogen; or $C_1$-$C_{22}$alkyl; or hydroxy-$C_1$-$C_{22}$alkyl; or $R_1$ and $R_2$ together with the nitrogen atom are linked together to form a piperidyl or morpholinyl radical;

$R_3$ is a —(C=O)$OR_6$ group; or a —(CO)$NHR_6$ group;

$R_6$ is $C_1$-$C_{22}$alkyl, which may be substituted by one or more than one —OH;

$R_4$ and $R_5$ are hydrogen; or $R_4$ and $R_5$ are linked together to form a carbocyclic ring which contains 6 carbon atoms.

Most preferred are compounds of formula (1), wherein $R_1$ and $R_2$ independently of each other are hydrogen; or hydroxy-$C_1$-$C_{22}$alkyl; wherein at least one of $R_1$ and $R_2$ is hydroxy-$C_1$-$C_{22}$alkyl;

$R_3$ is a —(C=O)$OR_6$ group; or a —(C=O)$NHR_6$ group;

$R_6$ is $C_1$-$C_{22}$alkyl; and $R_4$ and $R_5$ are hydrogen; or $R_4$ and $R_5$ are linked together to form a carbocyclic ring which contains 6 carbon atoms.

Most preferred are compounds of formula (2), wherein $R_7$ and $R_8$ independently of each other are hydrogen or $C_1$-$C_8$alkyl, which is optionally interrupted by one or more than one —O—;

A is —O—; or —NH;

$R_{11}$ is $C_1$-$C_{22}$alkyl; and $R_9$ and $R_{10}$ are hydrogen; or $R_9$ and $R_{10}$ are linked together to form a carbocyclic ring which contains 6 carbon atoms.

Most preferred are compounds of formula (2), wherein $R_7$ and $R_8$ together with the nitrogen atom form a morpholinyl or piperidyl radical;

A is —O—; or —NH;

$R_{11}$ is $C_1$-$C_{22}$alkyl; which is interrupted by one or more than one —O—; and $R_9$ and $R_{10}$ are hydrogen; or $R_9$ and $R_{10}$ are linked together to form a carbocyclic ring which contains 6 carbon atoms.

Even more preferred are compounds of formula (2), wherein $R_{11}$ is a radical of formula (1a) —$(CH_2)_m$—O—$R_{12}$, wherein $R_{12}$ is $C_1$-$C_4$alkyl; or $C_1$-$C_4$alkoxy-$C_1$-$C_3$alkyl;

m is a number from 1 to 3;

$R_7$ and $R_8$, independently of each other are hydrogen; $C_1$-$C_{12}$alkyl, which is optionally interrupted by one or more than one O; or $R_7$ and $R_8$ together with the nitrogen atom form a morpholinyl or piperidyl radical;

$R_9$ and $R_{10}$ are hydrogen; or form a carbocyclic ring which contains 6 carbon atoms; and A is —O—; or —NH.

The merocyanine compounds of the invention may be in the E/E-, E/Z- or Z/Z-geometrical isomer forms.

Alkyl, cycloalkyl, alkenyl, alkylidene or cycloalkenyl may be straight, chained or branched, monocyclic or polycyclic.

$C_1$-$C_{22}$alkyl is for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

Hydroxy-substituted alkyl is for example hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl.

$C_2$-$C_{22}$alkenyl is for example straight-chain $C_2$-$C_{12}$alkenyl or preferably branched $C_3$-$C_{12}$alkenyl. $C_1$-$C_{12}$alkyl, like vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the different isomers of hexenyl, octenyl, nonenyl, decenyl or dodecenyl.

$C_3$-$C_{12}$cycloalkyl is for example cyclopropyl, cyclobutyl, cyclopentyl, trimethylcyclohexyl or preferably cyclohexyl.

Examples of merocyanines according to the present invention are listed in Table A:

TABLE A

| Compound | Structure | Compound | Structure |
|---|---|---|---|
| MC01 | 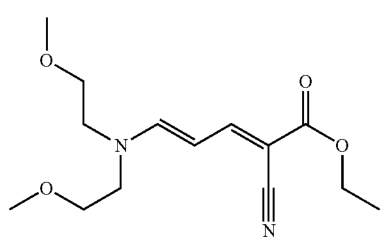 [SMILES: CCOC(=O)/C(C#N)=C/C=C/N(CCOC)CCOC] | MC02 | 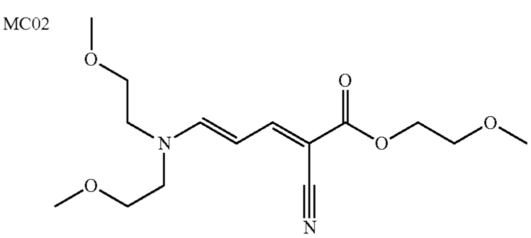 |

TABLE A-continued

| Compound | Structure | Compound | Structure |
| --- | --- | --- | --- |
| MC03 | 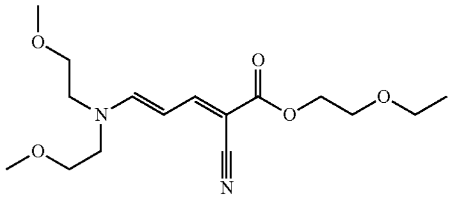 [SMILES: CCOCCOC(=O)/C(C#N)=C/C=C/N(CCOC)CCOC] | MC04 | 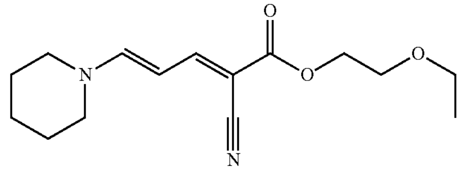 [SMILES: CCOCCOC(=O)/C(C#N)=C/C=C/N1CCCCC1] |
| MC05 | 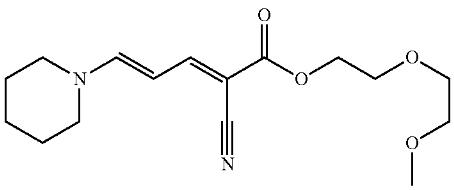 [SMILES: COCCOCCOC(=O)/C(C#N)=C/C=C/N1CCCCC1] | MC06 | 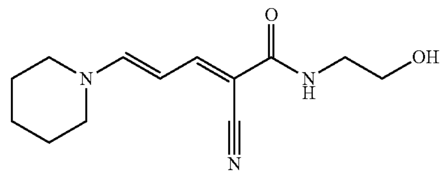 [SMILES: N#C/C(=C\C=C\N1CCCCC1)C(=O)NCCO] |
| MC07 | 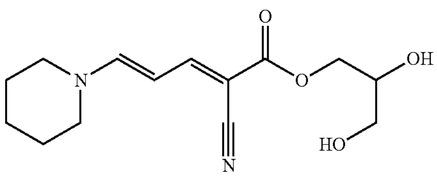 [SMILES: N#C/C(=C\C=C\N1CCCCC1)C(=O)OCC(O)CO] | MC08 | 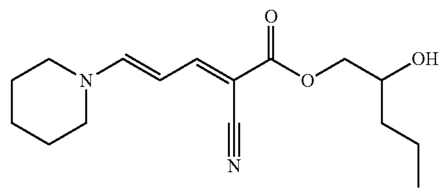 [SMILES: CCCC(O)COC(=O)/C(C#N)=C/C=C/N1CCCCC1] |
| MC09 | 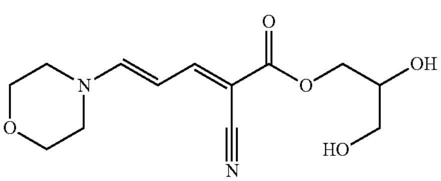 [SMILES: N#C/C(=C\C=C\N1CCOCC1)C(=O)OCC(O)CO] | MC10 | 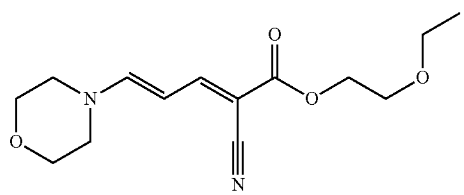 [SMILES: CCOCCOC(=O)/C(C#N)=C/C=C/N1CCOCC1] |
| MC11 | 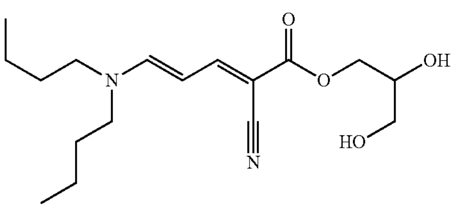 [SMILES: CCCCN(/C=C/C=C(\C#N)C(=O)OCC(O)CO)CCCC] | MC12 | 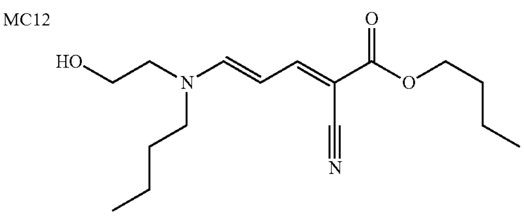 |
| MC13 | 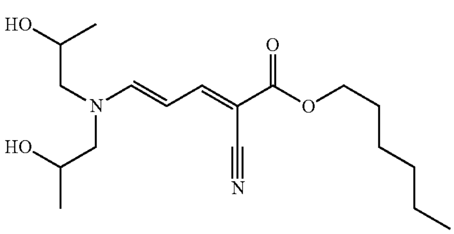 [SMILES: CCCCCCOC(=O)/C(C#N)=C/C=C/N(CC(C)O)CC(C)O] | MC14 | 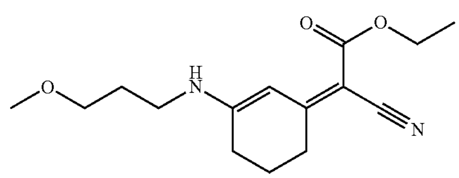 [SMILES: CCOC(=O)/C(C#N)=C1\C=C(NCCCOC)CCC1] |
| MC15 | 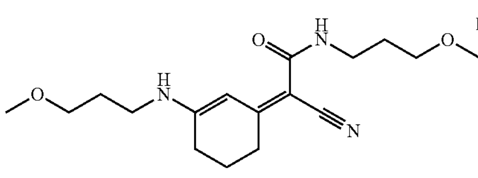 | MC16 | 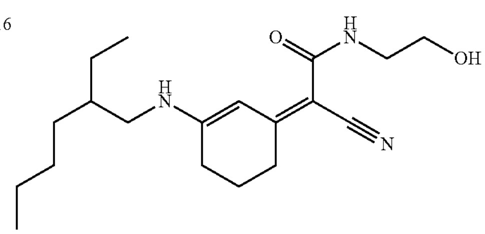 |

TABLE A-continued

| Compound | Structure | Compound | Structure |
|---|---|---|---|
| MC17 | 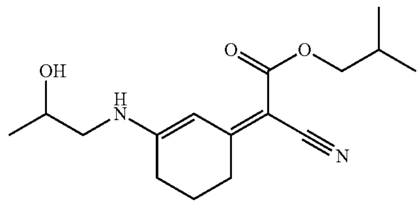 [SMILES: CC(C)COC(=O)/C(C#N)=C1\C=C(NCC(C)O)CCC1] | MC18 | 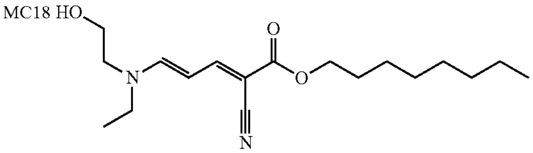 |
| MC19 | 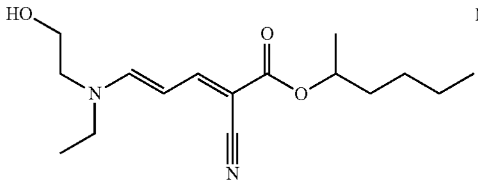 | MC20 | 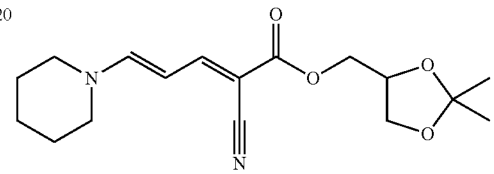 |
| MC21 | 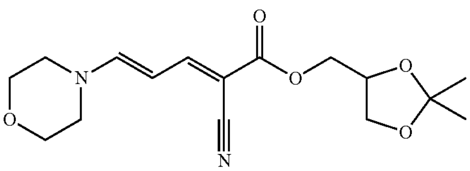 [SMILES: CC1(C)OCC(COC(=O)/C(C#N)=C/C=C/N2CCOCC2)O1] | MC22 | 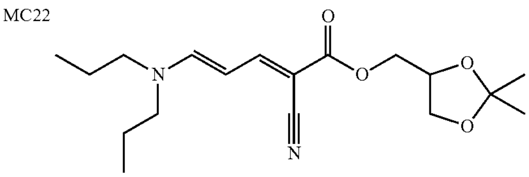 |
| MC23 | 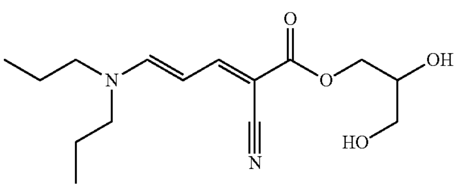 [SMILES: CCCN(/C=C/C=C(\C#N)C(=O)OCC(O)CO)CCC] | MC24 | 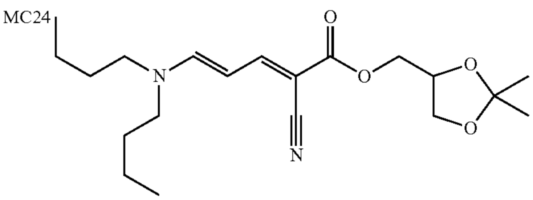 |
| MC25 | 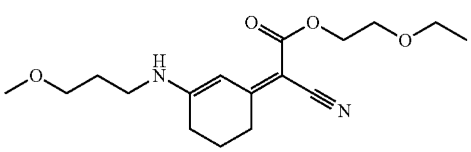 [SMILES: CCOCCOC(=O)/C(C#N)=C1\C=C(NCCCOC)CCC1] | MC26 | 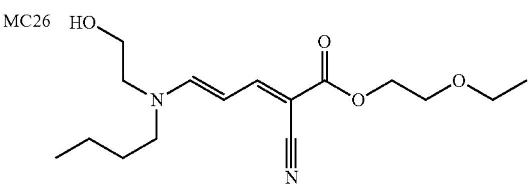 |
| MC27 | 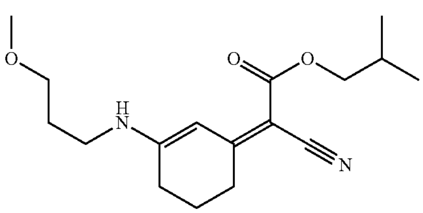 [SMILES: COCCCNC1=C/C(=C(/C#N)C(=O)OCC(C)C)CCC1] | MC28 | 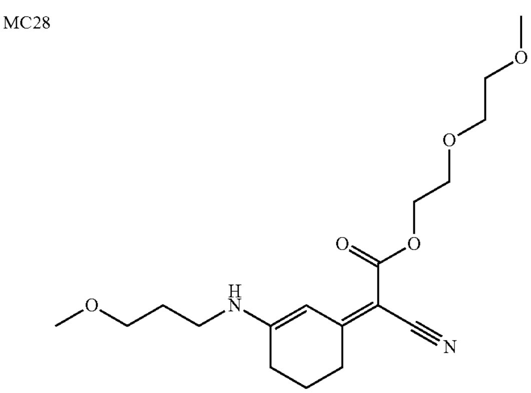 |

TABLE A-continued

| Compound | Structure | Compound | Structure |
|---|---|---|---|
| MC29 | 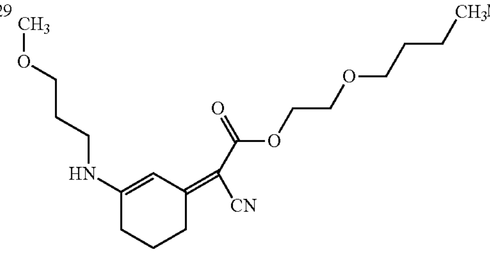 | MC30 | 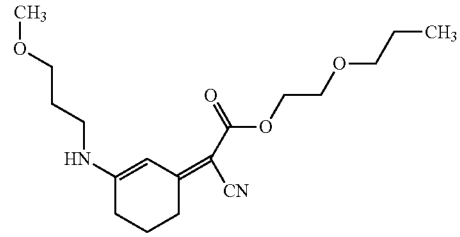 [SMILES: CCCOCCOC(=O)/C(C#N)=C1\C=C(NCCCOC)CCC1] |
| MC31 | 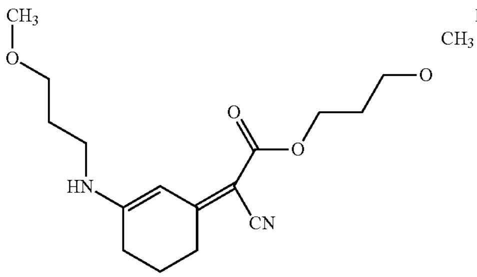 | MC32 | ALogP: 0.4823 |
| MC33 | ALogP: −0.2708 | MC34 | ALogP: 0.442 |
| MC35 | ALogP: 0.8451 | MC36 | ALogP: 1.005 |
| MC37 | 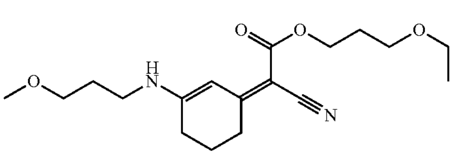 [SMILES: CCOCCCOC(=O)/C(C#N)=C1\C=C(NCCCOC)CCC1] | MC38 | 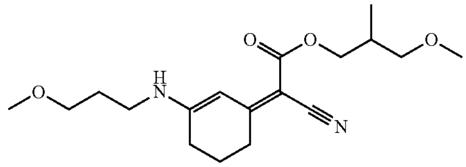 |

TABLE A-continued

| Compound | Structure | Compound | Structure |
|---|---|---|---|
| MC39 | 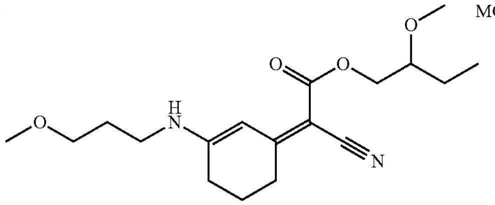 | MC40 | 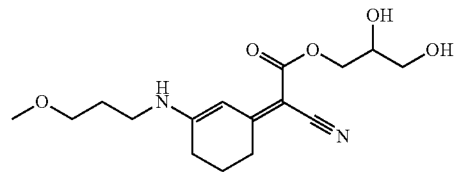 [SMILES: COCCCNC1=C/C(=C(/C#N)C(=O)OCC(O)CO)CCC1] |
| MC41 | 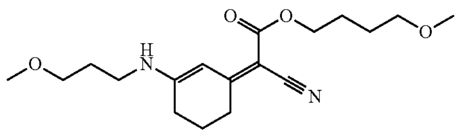 | MC42 | 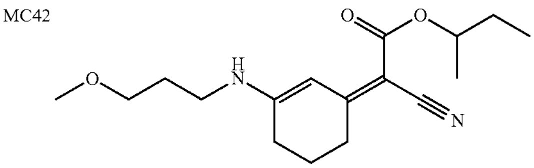 |
| MC43 | 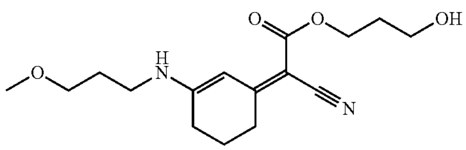 [SMILES: COCCCNC1=C/C(=C(/C#N)C(=O)OCCCO)CCC1] | MC44 | 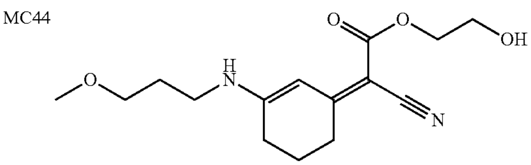 |
| MC45 | 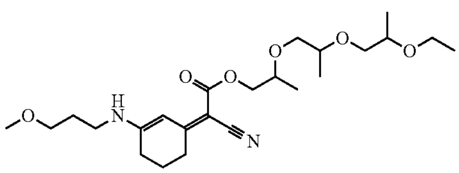 [SMILES: CCOC(C)COC(C)COC(C)COC(=O)/C(C#N)=C1\C=C(NCCCOC)CCC1] | MC46 | 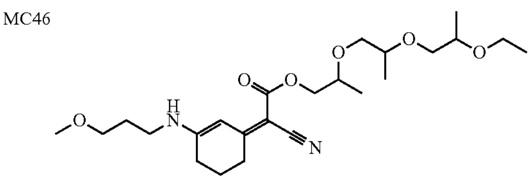 |
| MC47 | 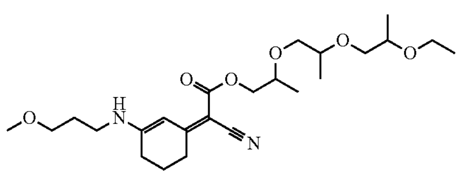 [SMILES: CCOC(C)COC(C)COC(C)COC(=O)/C(C#N)=C1\C=C(NCCCOC)CCC1] | | |

The most preferred merocyanine derivatives of the invention are selected in the group of the following compounds and their E/E-, E/Z- or Z/Z-geometrical isomer forms:

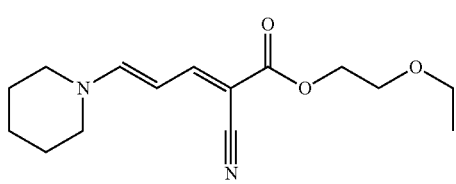

MC04

2-ethoxyethyl (2E, 4E)-2-cyano-5-(piperidin-1-yl)penta-2,4-dienoate

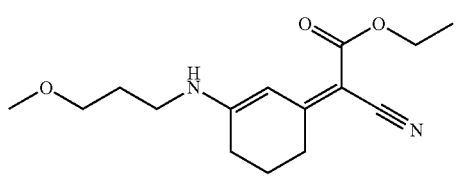

MC14 ethyl (2Z)-cyano{3-[(3-methoxypropyl)amino]cyclohex-2-en-1-ylidene}-ethanoate

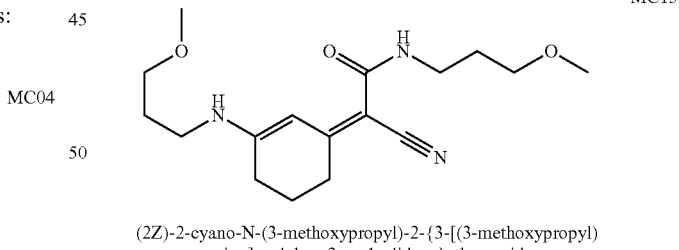

MC15

(2Z)-2-cyano-N-(3-methoxypropyl)-2-{3-[(3-methoxypropyl)amino]cyclohex-2-en-1-ylidene}ethanamide

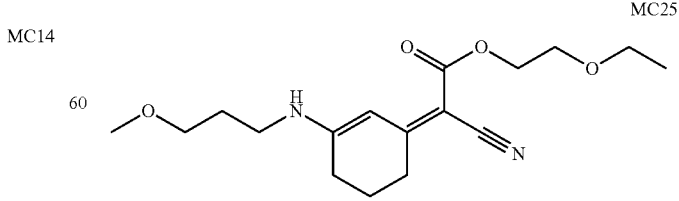

MC25

2-ethoxyethyl (2Z)-cyano{3-[(3-methoxypropyl)amino]cyclohex-2-en-1-ylidene}-ethanoate -continued

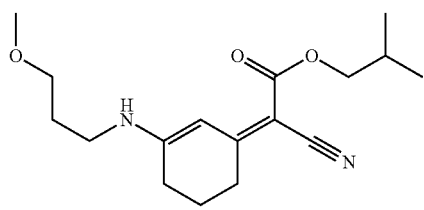

MC27

2-methylpropyl (2Z)-cyano{3-[(3-methoxypropyl)amino]cyclohex-2-en-1-ylidene}ethanoate

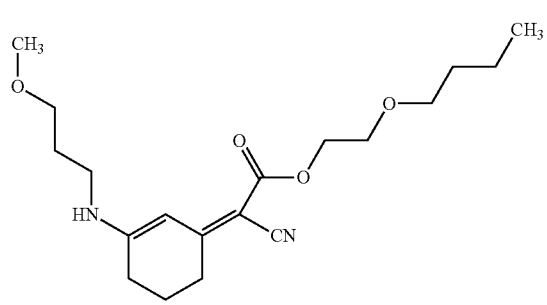

MC29

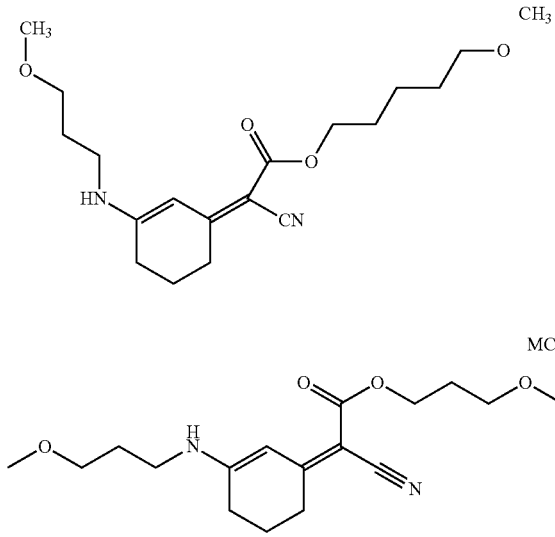

MC31

MC37

Very most preferred is 2-ethoxyethyl(2Z)-cyano{3-[(3-methoxypropyl)amino]cyclohex-2-en-1-ylidene}ethanoate in its E/E and/or its E/Z geometrical isomer corresponding to the formula

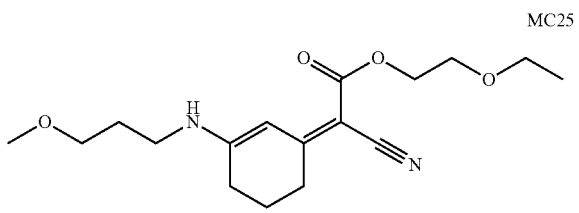 [SMILES: CCOCCOC(=O)/C(C#N)=C1\C=C(NCCCOC)CCC1]

MC25

The E/Z form has the following structure:

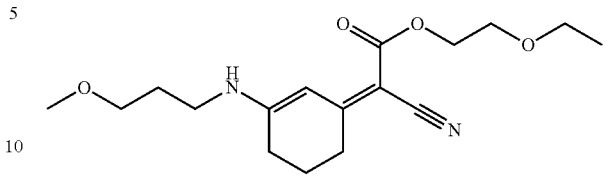

MC25(a)

The E/E form has the following structure:

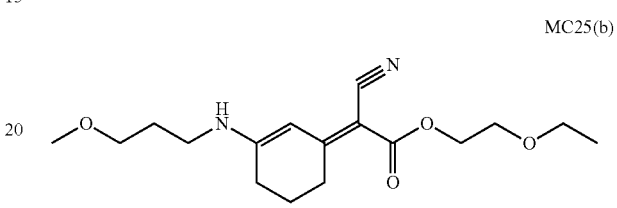

MC25(b)

The Applicant discovered that those particular compounds have the following properties: better chemical stability after 2 months at 45° C. in ethanol/water 1/1 mixture at 0.5% of concentration, a less yellow coloring.

The compounds of formula (1) and (2) are novel. They may be prepared according to known processes, as disclosed for example in J. Org. Chem. USSR (Engl. Transl.) 26(8), p. 1562f (1990); J. Heterocycl. Chem. 33(3), p. 763-766 (1996); Khimiya Geterotsiklicheskikh Soedinenii 11, p. 1537-1543 (1984); Khimiya Geterotsiklicheskikh Soedinenii 3, p. 397-404 (1982); Chem. Heterocycl. Comp. (Engl. Transl.) 24(8), 914-919 (1988) and in Synthetic Communications Vol. 33, No. 3, 2003, p 367-371.

The synthesis of the compounds used in the present invention is also disclosed in US2003/0181483A1, WO 0234710, Eur. J. Org. Chem. 2003, 2250-2253, J. Med. Chem. 1996, 39, 1112-1124 and J. Org. Chem., Vol. 37, No. 8, 1972, 1141-1145 as follows:

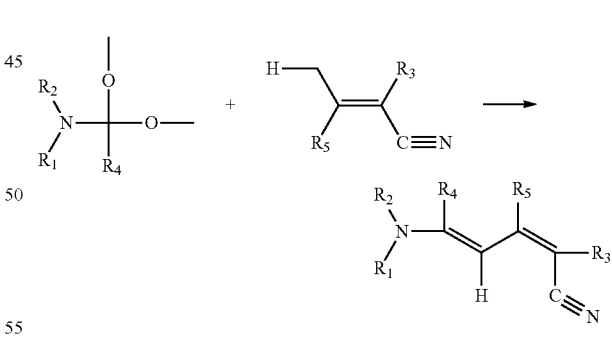

Vinylogene CH-acid compounds are reacted with acetales of amides.

In J. Heterocyclic Chem., 27, 1990, 1143-1151 aminoacrylic acid esters or aminoacrylnitriles are reacted with ethoxymethylenecyanoacetates in ethanol to the corresponding compounds used in the present invention.

Compounds of formula (1) and (2) wherein $R_4$ and $R_5$ or $R_9$ and $R_{10}$ together form a carbocyclic ring containing 6 C atoms, respectively, may be prepared according to procedures in WO 2007/071582, in IP.com Journal (2009), 9(5A), 29-30 under the title "Process for producing 3-amino-2-cyclohexan-1-ylidene compounds" and in U.S. Pat. No. 4,749,643 on col, 13, line 66-col. 14, line 57 and the references cited therein.

The merocyanines of formula

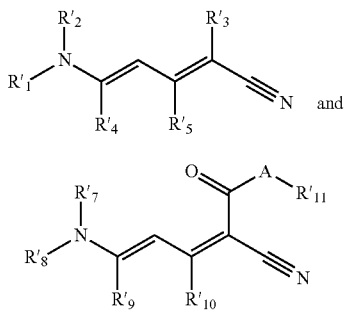

(1')

(2')

and/or its E/E-, E/Z- or Z/Z-geometrical isomer forms, wherein $R'_1$ and $R'_2$ independently of each other are hydrogen; $C_1$-$C_{22}$alkyl, $C_2$-$C_{22}$alkenyl, $C_2$-$C_{22}$alkinyl, which are optionally substituted by at least one hydroxy; or $R_1$ and $R_2$ together with the nitrogen atom linking them form a —$(CH_2)_n$— ring which is optionally interrupted by —O— or by —NH—;

$R'_3$ is a —(C=O)$OR'_6$ group; or a —(CO)$NHR'_6$ group;

$R'_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;

$R'_4$ and $R'_5$ are hydrogen; or $R'_4$ and $R'_5$ form a —$(CH_2)_n$— ring which is optionally substituted by $C_1$-$C_4$alkyl and/or interrupted by —O— or by —NH—;

n is a number from 2 to 7;

$R'_7$ and $R'_8$ independently of each other are hydrogen; $C_1$-$C_{22}$alkyl, $C_2$-$C_{22}$alkenyl, $C_2$-$C_{22}$alkinyl, which is optionally interrupted by one or more than one O and/or substituted by one or more than one OH; or $R'_7$ and $R'_8$ together with the nitrogen atom linking them form a —$(CH_2)_n$— ring which is optionally interrupted by —O—;

$R'_9$ and $R'_{10}$ are hydrogen; or $R'_9$ and $R'_{10}$ form a —$(CH_2)_n$— ring which is optionally substituted by $C_1$-$C_4$alkyl and/or interrupted by —O— or by —NH—;

A is —O—; or —NH;

$R'_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O; are particularly suitable for protecting household products against photolytic degradation.

Preferably compounds of formula (1') or (2') are used wherein at least one of $R_1$, $R_2$, $R_3$ and $R_6$, $R_7$ and $R_8$, or $R_{11}$ is substituted by hydroxy; and/or interrupted by one or more than one —O—.

"Household products" in the sense of the present invention are those products which are outside cosmetic personal care applications.

Examples of compounds of formula (1') and (2') are those listed in Table A and the compound

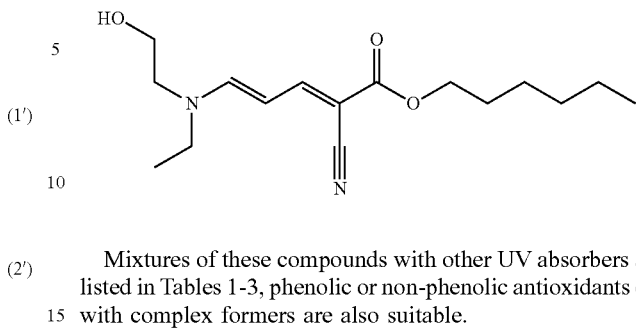

MC37

Mixtures of these compounds with other UV absorbers as listed in Tables 1-3, phenolic or non-phenolic antioxidants or with complex formers are also suitable.

Examples of organic UV filters that can be used in admixture with the compounds of formulas (1') and (2') are listed in the following Table:

TABLE 1

Suitable UV filter substances which can be additionally used with the compounds of formula (1') and/or (2')

p-aminobenzoic acid derivatives, for example 4-dimethylaminobenzoic acid
2-ethylhexyl ester;
salicylic acid derivatives, for example salicylic acid 2-ethylhexyl ester;
benzophenone derivatives, for example 2-hydroxy-4-methoxybenzophenone
and its 5-sulfonic acid derivative;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives,
described in EP-A-582 189, U.S. Pat. No. 5,338,539, U.S. Pat. No. 5,518, 713
and EP-A-613 893; polymeric UV absorbers, for example the benzylidene malonate derivatives described in EP-A-709 080;
camphor derivatives, for example 3-(4'-methyl)benzylidene-bornan-2-one, 3-benzylidene-bornan-2-one, N-[2(and 4)-2-oxyborn-3-ylidene-methyl)-benzyl]-acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts;
camphorbenzalkonium methosulfate;
hydroxyphenyltriazine compounds, for example 2-(4'-methoxyphenyl)-4,6-bis-(2'-hydroxy-4'-n-octyloxyphenyl)-1,3,5-triazine; 2,4-bis{[4-(3-(2-propyloxy)-2-hydroxyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis-{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in U.S. Pat. No.
5,332,568, EP-A-517 104, EP-A-507 691, WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane as described in CAS 9004-73-3), dimethicone, isopropyl titanium triisostearate
(as described in CAS 61417-49-0), metal soaps as magnesium stearate as described in CAS 4086-70-8), perfluoroalcohol phosphate as C9-15 fluoroalcohol phosphate (as described in CAS 74499-44-8; JP 5-86984, JP 4-330007)). The primary particle size is an average of 15 nm-35 nm and

TABLE 1-continued

Suitable UV filter substances which can be additionally used with the compounds of formula (1') and/or (2')

the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N. J. Lowe, N. A. Shaath,
Marcel Dekker, Inc., New York and Basle or in Cosmetics & Toiletries (107), 50ff (1992) also can be used as additional UV protective substances.

TABLE 2

Suitable UV filter substances which can be additionally used with the merocyanines of formula (1') and (2')

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485A1 | Formula 1 on p 2; Ex 1-4 on p 13; |
| DE102004039281A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800 274 B2 | Formulas I-VI and IX-XII on pp 14-18 |
| U.S. Pat. No. 6,890 520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formulas 1-2 on p 2; formula 3-4 on p 6; |
| U.S. Pat. No. 6,962,692 B2 | Formulas VII and VIII on p 6; Formulas I, II, IV-VI, IX, X on pp 14-16; Formula III on p 19 |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |

TABLE 2-continued

Suitable UV filter substances which can be additionally used with the merocyanines of formula (1') and (2')

| | |
|---|---|
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UV0 on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

TABLE 3

Suitable UV filter substances and adjuvants which can be additionally used with the compounds of formula (1') and/or (2')

| No. | Chemical Name | CAS No. |
|---|---|---|
| 1 | (+/−)-1,7,7-trimethyl-3-[(4-methylphenyl)methylene]bicyclo[2.2.1]-heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethylamino)benzoate | 21245-02-3 |
| 32 | 2-ethylhexyl salicylate | 118-60-5 |
| 33 | Benzole acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethylbutyl)-phenol]; Tinosorb M | 103597-45-1 |
| 46 | 2,4-bis{[4-(2-ethylhexyloxy)-2-hydroxy-phenyl}-6-(4-methoxy-phenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[(1,1-dimethylethyl)amino]car-bonyl]phenyl]amino]1,3,5-triazine-2,4-diyl]diimino]bis-, bis(2-ethylhexyl)ester; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |

TABLE 3-continued

Suitable UV filter substances and adjuvants which can be additionally used with the compounds of formula (1') and/or (2')

| No. | Chemical Name | CAS No. |
|---|---|---|
| 53 | 1-Dodecanaminium, N-[3-[[4-(dimethylamino)benzoyl]amino]-propyl]N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-α-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N"-(2-ethylhexyl)- or Uvasorb K2A | 288254-16-0 |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga *porphyra umbilicalis* (INCI: *Porphyra Umbilicalis*) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 77 | Pentanenitrile, 2-[2,3-dihydro-5-methoxy-3,3-dimethyl-6-[(2-methyl-2-propenyl)oxy]-1H-inden-1-ylidene]-4,4-dimethyl-3-oxo- | 425371-15-9 |
| 78 | Pentanenitrile, 2-(2,3-dihydro-6-hydroxy-5-methoxy-3,3-dimethyl-1H-inden-1-ylidene)-4,4-dimethyl-3-oxo- | 425371-14-8 |
| 79 | Benzenepropanenitrile, α-(2,3-dihydro-3,3,5-trimethyl-1H-inden-1-ylidene)-β-oxo- | 425371-11-5 |
| 80 | Cyclohexanepropanenitrile, α-[5-(1,1-dimethylethyl)-2,3-dihydro-3,3-dimethyl-1H-inden-1-ylidene]-1-methyl-β-oxo- | 425371-10-4 |
| 81 | Pentanenitrile, 2-[6-(acetyloxy)-2,3-dihydro-5-methoxy-3,3-dimethyl-1H-inden-1-ylidene]-4,4-dimethyl-3-oxo- | 425371-09-1 |
| 82 | Pentanenitrile, 2-[2,3-dihydro-5-methoxy-3,3-dimethyl-6-[2-methyl-3-[1,3,3,3-tetramethyl-1-[(trimethylsilyl)oxy]disiloxanyl]propoxy]-1H-inden-1-ylidene]-4,4-dimethyl-3-oxo- | 425371-08-0 |
| 83 | Pentanenitrile, 2-(2,3-dihydro-5-methoxy-3,3,6-trimethyl-1H-inden-1-ylidene)-4,4-dimethyl-3-oxo- | 425371-07-9 |
| 84 | Pentanenitrile, 4,4-dimethyl-3-oxo-2-(2,3,7,8-tetrahydro-8,8-dimethyl-6H-indeno[5,6-b]-1,4-dioxin-6-ylidene)- | 425371-06-8 |
| 85 | Pentanenitrile, 2-(2,3-dihydro-3,3,6-trimethyl-1H-inden-1-ylidene)-4,4-dimethyl-3-oxo- | 425371-05-7 |
| 86 | Pentanenitrile, 2-(2,3-dihydro-3,3,5,6-tetramethyl-1H-inden-1-ylidene)-4,4-dimethyl-3-oxo- | 425371-04-6 |
| 87 | Pentanenitrile, 2-(2,3-dihydro-5-methoxy-3,3,4,6-tetramethyl-1H-inden-1-ylidene)-4,4-dimethyl-3-oxo- | 425371-03-5 |
| 88 | Pentanenitrile, 2-(2,3-dihydro-5,6-dimethoxy-3,3-dimethyl-1H-inden-1-ylidene)-4,4-dimethyl-3-oxo- | 261356-13-2 |
| 89 | Benzoic Acid, 2-[4-(Diethylamino)-2-Hydroxybenzoyl]-, Hexyl Ester; UVINUL A+ | 302776-68-7 |
| 90 | 2-Ethylhexyl 4-methoxycinnamate; UVINUL MC 80 | 5466-77-3 |
| 91 | 2-Propenoic acid, 3-(4-methoxyphenyl)-, 3-methylbutyl ester; | 71617-10-2 |
| 92 | Phenol, 2-(2H-benzotriazol-2-yl)-6-dodecyl-4-methyl-; TINOGARD TL | 23328-53-2 |

The compounds of formulas (1') and (2') may also be used in admixture with phenolic or lactone-type antioxidants as disclosed for example in WO00/25731 or with hindered amine light stabilizers as disclosed in WO 03/103622, e.g. hindered nitroxyl, hydroxylamine and hydroxylamine salt compounds.

The stabilizer systems of the present invention are preferably used in household cleaning and treatment agents, for example in laundry products and fabric softeners, liquid cleansing and scouring agents, glass detergents, neutral cleaners (all-purpose cleaners), acid household cleaners (bath), bathroom cleaners, WC cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multi-purpose polishes and leather and vinyl dressing agents (leather and vinyl sprays) and air fresheners.

Household cleaning agents are aqueous or alcoholic (ethanol or isopropyl alcohol) solutions of one or more of the following components:
  anionic, nonionic, amphoteric and/or cationic surfactants
  soaps, prepared by saponification of animal and vegetable greases
  organic acids, like hydrochloric acid, phosphoric acid, or sulfuric acid,
  for basic products inorganic (NaOH or KOH) or organic bases;
  abrasives for improved cleaning of surfaces,
  waxes and/or silicones for maintenance and protection of surfaces,
  polyphosphates,
  substances which eliminate hypochlorite or halogens;
  peroxides comprising bleaching activators like TAED, for example sodium perborate or $H_2O_2$;
  enzymes;
  in washing detergents discoloration inhibitors, soil-release compounds, grey scale inhibitors, foam inhibitors, fluorescent whitening agents;
  cleaning agents based on wax may comprise solvents selected from benzine, turpentine and/or paraffins and emulsifiers based on wax;
  filling agents like silicates, polyphosphates, Zeolithes for powdery cleaning agents;
  pigments, lakes or soluble dyes;
  perfumes; and
  light stabilizers, antioxidants and chelating agents.
Colored cleaning agents can comprise the following dyes:
  inorganic pigments, for example iron oxide (Iron Oxide Red, Iron Oxide Yellow, Iron Oxide Black, etc.), Ultramarines, Chromium Oxide Green or Carbon Black;
  natural or synthetic organic pigments;
  disperse dyes which may be solubilized in solvents like direct hair dyes of the HC type, for example HC Red No. 3, HC Blue No. 2 and all other hair dyes listed in International Cosmetic Ingredient Dictionary and Handbook, 7th edition 19997) or the dispersion dyes listed in Color Index International or Society of Dyers and Colourists;
  color varnishes (insoluble salts of soluble dyes, like many Ca-, Ba- or Al-salts of anionic dyes);
  soluble anionic or cationic dyes, like acid dyes (anionic), basic dyes (cationic), direct dyes, reactive dyes or solvent dyes.

Generally, for the coloration of household products all substances are suitable which have an absorption in the visible light of electromagnetic radiation (wave length of ca. 4000 to 700 nm). The absorption is often caused by the following chromophores: Azo-(mono-, di, tris-, or poly-) stilbene-, carotenoide-, diarylmethane-, triarylmethane-, xanthene-, acridine-, quinoline, methine- (also polymethin-), thiazole-, indamine-, indophenol-, azin-, oxazine, thiazin-, anthraquinone-, indigoid-, phtalocyanine- and further synthetic, natural and/or inorganic chromophores.

The present invention also relates to home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

Typical examples of household cleaning and treating agents are listed in the table below:

| Household cleaners/ household treating agents | Ingredients |
|---|---|
| detergent concentrate | surfactant mixture, ethanol, antioxidant, water, UV absorbers, antioxidants |
| shoe polish wax | wax emulsifier, antioxidant, water, preservative, UV absorbers, antioxidants |
| wax-containing floor cleaning agent | emulsifier, wax, sodium chloride, merocyanines of formulae (1') and/or (2'), water, preservative UV absorbers, antioxidant |

The stabilizers of formula (1') and/or (2') according to the present invention are for example incorporated by dissolution in an oil phase or alcoholic or water phase, where required at elevated temperature.

The present household products have high stability towards color changes and chemical degradation of the ingredients present in these products. For example, present compositions that comprise a dye are found to have excellent color stability.

Furthermore, the merocyanines of the formulas (1') and (2') can be used as additives in organic materials, preferably natural or synthetic organic polymers.

Examples of organic polymers are
1. Polymers of monoolefins and diolefins,
2. Mixtures of the polymers mentioned under 1),
3. Copolymers of monoolefins and diolefins with each other or with other vinyl monomers,
4. Hydrocarbon resins (for example $C_5$-$C_9$) including hydrogenated modifications thereof (e.g. tackifiers) and mixtures of polyalkylenes and starch.
5. Polystyrene, poly(p-methylstyrene), poly(α-methylstyrene).
6. Aromatic homopolymers and copolymers derived from vinyl aromatic monomers
6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof,
6b. Hydrogenated aromatic polymers derived from hydrogenation of polymers mentioned under 6.),
6c. Hydrogenated aromatic polymers derived from hydrogenation of polymers mentioned under 6a.).
7. Graft copolymers of vinyl aromatic monomers 8. Halogen-containing polymers especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from α,β-unsaturated acids and derivatives thereof
10. Copolymers of the monomers mentioned under 9) with each other or with other unsaturated monomers,
11. Polymers derived from unsaturated alcohols and amines or the acyl derivatives or acetals thereof, as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams,
17. Polyureas, polyimides, polyamide-imides, polyetherimides, polyesterimides, polyhydantoins and polybenzimidazoles.
18. Polyesters derived from dicarboxylic acids and diols and/or from hydroxycarboxylic acids or the corresponding lactones or lactides, as well as copolyether esters derived from hydroxyl-terminated polyethers, and also polyesters modified with polycarbonates or MBS.
19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatine and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
30. Naturally occurring and synthetic organic materials which are pure monomeric compounds or mixtures of such compounds,
31. Aqueous emulsions of natural or synthetic rubber, e.g. natural latex or latices of carboxylated styrene/butadiene copolymers.

The organic material is preferably a synthetic polymer, in particular from one of the above groups. A polyolefin homo- or copolymer is preferred. Polyethylene, polypropylene, a polyethylene copolymer or a polypropylene copolymer are particularly preferred.

Of interest is also ethylene/propylene/diene elastomer (EPDM).

The compound of the formulas (1') and/or (2') may be present in the organic material in an amount of preferably 0.005 to 5%, in particular 0.01 to 1% or 0.05 to 1%, relative to the weight of the organic material.

The compound of the formulas (1') and (2') can be incorporated into the organic material to be stabilized by known methods, for example before or during shaping or by applying the dissolved or dispersed stabilizer to the organic material, if necessary with subsequent evaporation of the solvent. The stabilizer can be added to the organic material in the form of a powder, granules or a master batch, which contains said stabilizer in, for example, a concentration of from 2.5 to 25% by weight.

The materials stabilized according to this invention can be used in a wide variety of forms, for example as films, fibres, tapes, moulding compositions, profiles or as binders for paints, adhesives or putties.

The Plastics According to the Present Invention May be Used for the Preparation of:

II-3) Devices for the electronic industry, in particular insulation for plugs, especially computer plugs, cases for electric and electronic parts, printed boards, and materials for electronic data storage such as chips, check cards or credit cards.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), BOPP, BOPET, bottles.

VI-2) Storage systems such as boxes (crates), luggage, chest, household boxes, pallets, shelves, tracks, screw boxes, packs, and cans.

VI-3) medical devices such as piston, ophthalmic applications, diagnostic devices, and packing for pharmaceuticals blister.

VII-4) Materials for optical and magnetic data storage.

VII-5) Kitchen ware (eating, drinking, cooking, storing).

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

Preferably the compounds of formula (1') and/or (2') are used for food and pharmaceutical packaging applications.

Any packaging article or structure intended to completely enclose a product will be deemed to have a "packaging wall," as that term is used herein, if the packaging article comprises a wall, or portion thereof, that is, or is intended to be, interposed between a packaged product and the atmosphere outside of the package and such wall or portion thereof comprises at least one layer incorporating the compounds of formula (1') and/or (2') according to the present invention. Thus, bowls, bags, liners, trays, cups, cartons, pouches, boxes, bottles and other vessels or containers which are intended to be sealed after being filled with a given product are covered by the term "packaging wall" if the compounds of formula (1') and/or (2') according to the present invention are present in any wall of such vessel (or portion of such wall) which is interposed between the packaged product and the outside environment when the vessel is closed or sealed. One example is where the compounds of formula (1') and/or (2') according to the present invention are fabricated into, or between, one or more continuous thermoplastic layers enclosing or substantially enclosing a product. Another example of a packaging wall according to the present invention is a monolayer or multilayer film containing the compounds of formula (1') and/or (2') used as a cap liner in a beverage bottle (i.e., for beer, wine, fruit juices, etc.) or as a wrapping material.

To prepare a packaging wall, the compounds of formula (1') and/or (2') are compounded into or otherwise combined with a suitable packaging resin whereupon the resulting resin formulation is fabricated into sheets, films or other shaped structures. Extrusion, co-extrusion, blow moulding, injection moulding and any other sheet, film or general polymeric melt-fabrication technique can be used. Sheets and films obtained from the compounds of formula (1') and/or (2') can be further processed, e.g. by coating or lamination, to form multilayered sheets or films, and then shaped, such as by thermoforming or other forming operations, into desired packaging walls in which at least one layer contains the compounds of formula (1') and/or (2') according to the present invention. Such packaging walls can be subjected to further processing or shaping, if desired or necessary, to obtain a variety of active-barrier end-use packaging articles. The present invention reduces the cost of such barrier articles in comparison to conventional articles which afford barrier properties using passive barrier films.

An example of a packaging article using the packaging wall described above is a two-layer or three-layer dual ovenable tray made of crystalline polyethylene terephthalate ("C-PET") suitable for packaging pre-cooked single-serving meals. In a three-layer construction, an oxygen-scavenging layer of 250 to 500 µm thickness is sandwiched between two non-scavenging C-PET layers of 70 to 250 µm thickness.

A primary application for the packaging walls, and packaging articles of the invention is in the packaging of perishable foods. For example, packaging articles utilizing the invention can be used to package milk, yogurt, ice cream, cheeses; stews and soups; meat products such as hot dogs, cold cuts, chicken, beef jerky; single-serving pre-cooked meals and side dishes; homemade pasta and spaghetti sauce; condiments such as barbecue sauce, ketchup, mustard, and mayonnaise; beverages such as fruit juice, wine, and beer; dried fruits and vegetables; breakfast cereals; baked goods such as bread, crackers, pastries, cookies, and muffins; snack foods such as candy, potato chips, cheese-filled snacks; peanut butter or peanut butter and jelly combinations, jams, and jellies; dried or fresh seasonings; and pet and animal foods; etc. The foregoing is not intended to be limiting with respect to the possible applications of the invention. Generally speaking, the invention can be used to enhance the barrier properties in packaging materials intended for any type of product which may degrade in the presence of oxygen.

Preferably the compounds of formula (1') and/or (2') are used for protection of UV-A sensitive drugs from photodegradation by incorporation of the compounds of formula (1') and/or (2') according to the present invention in transparent blister packs or transparent pharmacy containers.

"Blister pack" is a term for several types of pre-formed plastic packaging used for small consumer goods, foods, and for pharmaceuticals.

The primary component of a blister pack is a cavity or pocket made from a "formable" web, usually a thermoformed plastic. This usually has a backing of paperboard or a "lidding" seal of aluminum foil or plastic. A blister that folds onto itself is often called a clamshell.

Blister packs are commonly used as unit-dose packaging for pharmaceutical tablets, capsules or lozenges. Blister packs can provide barrier protection for shelf life requirements, and a degree of tamper resistance. Blister packs are the main packaging type since pharmacy dispensing and re-packaging are not common.

Other types of blister packs consist of carded packaging where goods such as toys, hardware, and electrical items are contained between a specially made paperboard card and clear pre-formed plastic such as PVC.

A hinged blister is known as a clamshell, used for a variety of products. It can be used as a security package to deter package pilferage for small high-value items, such as consumer electronics. It consists of one sheet folded over onto itself and sometimes fused at the edges.

Medical Blister trays differ from Pharmaceutical blister packs in that these are not push-through packs. The thermoformed base web is made of a thicker plastic sheet, generally between 500µ to 1000µ and cannot be collapsed, thus forming a solid tray. The lidding film provides a peel-open feature and is generally porous to allow sterilization. Such medical blister packs are used for medical devices, used in hospitals. The blisters are produced by thermoforming or cold forming processes.

In the case of thermoforming, a plastic film or sheet is unwound from the reel and guided though a pre-heating station on the blister line. The temperature of the pre-heating plates (upper and lower plates) is such that the plastic will soften and become pliable. The warm plastic will then arrive in a forming station where a large pressure (4 to 8 bar) will form the blister cavity into a negative mold. The mold is cooled such that the plastic becomes rigid again and maintains its shape when removed from the mold. In case of difficult shapes, the warm film will be physically pushed down partially into the cavity by a "plug-assist" feature. Plug-assist results in a blister cavity with more uniform wall distribution and is typically used when the cavity size and shape is larger than a small tablet.

In the case of cold forming, an aluminum-based laminate film is simply pressed into a mold by means of a stamp. The aluminum will be elongated and maintain the formed shape. In the industry these blisters are called cold form foil (CFF) blisters. The principal advantage of cold form foil blisters is that the use of aluminum offers a near complete barrier for water and oxygen, allowing an extended product expiry date. The principal disadvantages of cold form foil blisters are: the slower speed of production compared to thermoforming; the lack of transparency of the package (a therapy compliance disadvantage); and the larger size of the blister card (aluminum cannot be formed with near 90 degree angles).

The most basic material for the forming web is PVC or Polyvinyl Chloride. In the case of blister packaging the PVC sheet does not contain any plasticizer and is sometimes referred to as Rigid PVC or RPVC. Multi-layer blister films based on PVC are often used for pharmaceutical blister packaging, whereby the PVC serves as the thermoformable backbone of the structure.

Typical constructions used for pharmaceutical products are 250μ PVC film laminated to 15μ-100μ PCTFE film. Duplex structures are PVC/PCTFE and triplex laminates are PVC/PE/PCTFE. Deeper cavities can be formed by using the triplex structures with PE. Typical WVTR values are between 0.06-0.40 g/m2/day.

Other typical materials are cyclic olefin copolymers (COC) or polymers (COP) which can provide moisture barrier to blister packs, typically in multilayered combinations with polypropylene (PP), polyethylene (PE), or glycol-modified polyethylene terephthalate (PETg). Unlike PVC and other common pharmaceutical barrier resins, cyclic olefin resins do not contain chlorine or other halogens in their molecular structure, being comprised solely of carbon and hydrogen.

The compounds of formula (1') and/or (2') can also be used as additives for photographic and printing applications, for electronic applications and for protecting the ingredients in agriculture applications.

EXAMPLES

A. Preparation Examples of Merocyanine UV Absorbers

Example A1

Preparation of the Compound of Formula (101)

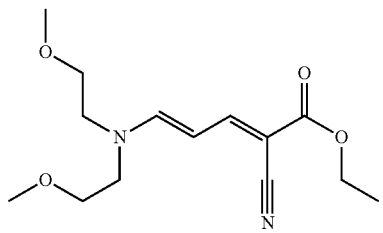

55.33 grams of bis-(2-methoxyethyl)amine are reacted with 1,1,3,3-tetramethoxypropane in acetic acid, concentrated and treated with 21.48 grams of ethyl cyanoacetate in the presence of an organic base and a solvent.

The following base/solvent combinations are used:

| Example | Base | Solvent |
| --- | --- | --- |
| Example A1.1 | DBU (1,8-diazabicyclo[5.4.0]undec-7-ene) | dimethylformamide |
| Example A1.2 | DBU (1,5-diazabicyclo[4.3.0]non-5-ene) | dimethylacetamide |
| Example A1.3 | DBN (1,5-diazabicyclo[4.3.0]non-5-ene) | 1-methylpyrrolidone |
| Example A1.4 | DBN (1,5-diazabicyclo[4.3.0]non-5-ene) | dimethylsulfoxide |
| Example A1.5 | DBU (1,8-diazabicyclo[5.4.0]undec-7-ene) | dimethylformamide |
| Example A1.6 | sodium methylate | dimethylacetamide |
| Example A1.7 | sodium methylate | isopropanol |
| Example A1.8 | potassium t-butoxide | t-butanol |

The reaction temperature is between 0° C. and the boiling point of the solvent.

The reaction end point is confirmed by thin layer chromatography or high performance liquid chromatography.

After the reaction, the product (101) is obtained from the reaction mixture through ordinary product isolation by liquid-liquid separation, column chromatography or crystallization by addition of a poor solvent to the reaction mixture.

The desired product (101) is obtained in yields of 66% (36 grams) as a dark brownish oil which crystallized as yellow crystals (Melting point: 76.9° C.).

Example A2

Preparation of the Compound of Formula (102)

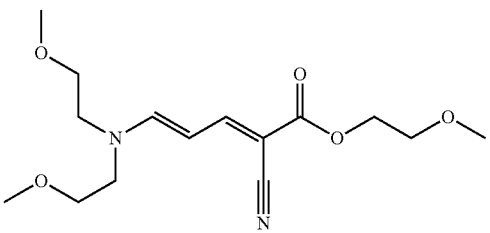

55.33 grams of bis-(2-methoxyethyl)amine are condensed with 1,1,3,3-tetramethoxypropane in acetic acid, concentrated and treated with 27.18 grams of 2-methoxyethyl-cyanoacetate in the presence of an organic base and a solvent.

The following base/solvent combinations are used:

| Example | Base | Solvent |
| --- | --- | --- |
| Example A2.1 | DBU (1,8-diazabicyclo[5.4.0]undec-7-ene) | dimethylformamide |
| Example A2.2 | DBN (1,5-diazabicyclo[4.3.0]non-5-ene) | dimethylacetamide |
| Example A2.3 | DBN (1,5-diazabicyclo[4.3.0]non-5-ene) | 1-methylpyrrolidone |
| Example A2.4 | DBN (1,5-diazabicyclo[4.3.0]non-5-ene) | dimethylsulfoxide |

-continued

| Example | Base | Solvent |
|---|---|---|
| Example A2.5 | DBU (1,8-diazabicyclo[5.4.0]undec-7-ene) | dimethylformamide |
| Example A2.6 | N-methylmorpholine | dimethylacetamide |
| Example A2.7 | bis-(2-methoxyethyl)amine | 1-methylpyrrolidone |
| Example A2.8 | sodium methylate | dimethylsulfoxide |

After the reaction, the product (102) is obtained from the reaction mixture through silica gel column chromatography (eluent: toluene/acetone).

The desired product (102) is obtained in yields of 75% (45.44 grams) as a yellow powder (melting point: 92.2° C.).

Example A3

Preparation of the Compound of Formula

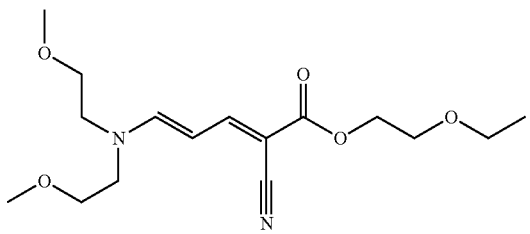

(103)

55.33 grams of bis-(2-methoxyethyl)amine are condensed with 1,1,3,3-tetramethoxypropane in acetic acid, concentrated and treated with 29.85 grams of 2-ethoxyethyl-cyanoacetate in the presence of an organic base and a solvent The following base/solvent combinations are used:

| Example | Base | Solvent |
|---|---|---|
| Example A3.1 | DBU (1,8-diazabicyclo[5.4.0]undec-7-ene) | dimethylformamide |
| Example A3.2 | DBN (1,5-diazabicyclo[4.3.0]non-5-ene) | dimethylacetamide |
| Example A3.3 | DBN (1,5-diazabicyclo[4.3.0]non-5-ene) | 1-methylpyrrolidone |
| Example A3.4 | DBN (1,5-diazabicyclo[4.3.0]non-5-ene) | dimethylsulfoxide |
| Example A3.5 | DBU (1,8-diazabicyclo[5.4.0]undec-7-ene) | dimethylformamide |
| Example A3.6 | N-methylmorpholine | dimethylacetamide |
| Example A3.7 | bis-(2-methoxyethyl)amine | 1-methylpyrrolidone |
| Example A3.8 | sodium methylate | dimethylsulfoxide |

After the reaction, the product (103) is obtained from the reaction mixture through ordinary product isolation by liquid-liquid separation, column chromatography or crystallization by addition of a poor solvent to the reaction mixture.

The desired product (103) is obtained in yields of 66% (39.99 grams) as beige crystals (melting point: 58.3° C.).

Example A4

Preparation of the Compound of Formula

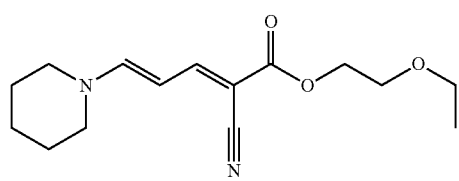

(104)

70.67 grams of piperidine are condensed with 1,1,3,3-tetramethoxypropane in acetic acid, concentrated and treated with 59.72 grams of 2-ethoxyethyl cyanoacetate cyanoacetate in the presence of an organic base and a solvent.

The following base/solvent combinations are used:

| Example | Base | Solvent |
|---|---|---|
| Example A4.1 | DBU (1,8-diazabicyclo[5.4.0]undec-7-ene) | dimethylformamide |
| Example A4.2 | DBN (1,5-diazabicyclo[4.3.0]non-5-ene) | dimethylacetamide |
| Example A4.3 | DBN (1,5-diazabicyclo[4.3.0]non-5-ene) | 1-methylpyrrolidone |
| Example A4.4 | DBN (1,5-diazabicyclo[4.3.0]non-5-ene) | dimethylsulfoxide |
| Example A4.5 | DBU (1,8-diazabicyclo[5.4.0]undec-7-ene) | dimethylformamide |
| Example A4.6 | piperidine | dimethylacetamide |
| Example A4.7 | piperidine | 1-methylpyrrolidone |
| Example A4.8 | sodium methylate | dimethylsulfoxide |

The desired product (104) is obtained in yields of 91% (96.5 grams) as an orange powder.

After silica gel column chromatography (eluent: toluene/acetone) the pure product (104) is obtained yielding dark yellow crystals.

Melting point: 66-67° C.

Example A5a

Preparation of Compound of Formula

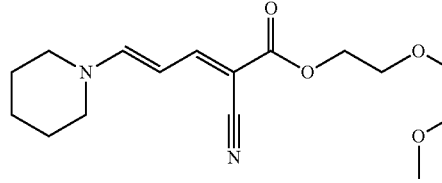

(105)

132.83 grams of piperidine are condensed with 1,1,3,3-tetramethoxypropane in acetic acid, concentrated and treated with 133.38 grams of 2-(2-methoxyethoxy)-ethyl-cyanoacetate in the presence of an organic base and a solvent.

The following base/solvent combinations are used:

| Example | Base | Solvent |
|---|---|---|
| Example A5a.1 | DBU (1,8-diazabicyclo[5.4.0]undec-7-ene | dimethylformamide |

| Example | Base | Solvent |
|---|---|---|
| Example A5a.2 | DBN (1,5-diazabicyclo[4.3.0]non-5-ene) | dimethylacetamide |
| Example A5a.3 | DBN (1,5-diazabicyclo[4.3.0]non-5-ene) | 1-methylpyrrolidone |
| Example A5a.4 | DBN (1,5-diazabicyclo[4.3.0]non-5-ene) | dimethylsulfoxide |
| Example A5a.5 | DBU (1,8-diazabicyclo[5.4.0]undec-7-ene) | dimethylformamide |
| Example A5a.6 | piperidine | dimethylacetamide |
| Example A5a.7 | piperidine | 1-methylpyrrolidone |
| Example A5a.8 | sodium methylate | dimethylsulfoxide |

The desired product (105) is obtained in yields of 38% (82.4 grams) as an dark oil.

After column chromatography over silica gel and toluene/acetone (9:1) as eluent the product (105) crystallizes from water as orange crystals. Melting point: 43.5-45° C.

Example A5b

Preparation of the Compound of Formula (105)

By using 5 grams of 3-(1-piperidinyl)-2-propenal and 7.39 grams of 2-(2-methoxyethoxy)ethyl-2-cyano acetic acid ester in the presence of a base and optionally a solvent the desired product is obtained in yields of 32% (3.5 grams) as an dark oil.

The following base/solvent combinations are used:

| Example | Base | Solvent |
|---|---|---|
| Example A5b.1 | piperidine | no solvent |
| Example A5b.2 | N-methylmorpholine | dimethylacetamide |
| Example A5b.3 | piperidine | 1-methylpyrrolidone |
| Example A5b.4 | piperidine | dimethylsulfoxide |

Example A6

Preparation of the Compound of Formula

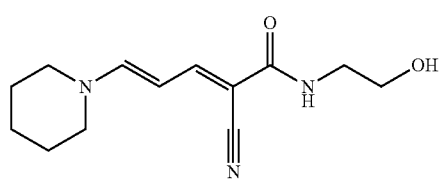

(106)

2.89 grams of piperidine are condensed with 1,1,3,3-tetramethoxypropane in acetic acid, concentrated and treated with 1.22 grams of 2-cyano-N-(2-hydroxyethyl)acetamide in the presence of an organic base and a solvent.

The following base/solvent combinations are used:

| Example | Base | Solvent |
|---|---|---|
| Example A6.1 | DBU (1,8-diazabicyclo[5.4.0]undec-7-ene) | dimethylformamide |
| Example A6.2 | DBN (1,5-diazabicyclo[4.3.0]non-5-ene) | dimethylacetamide |
| Example A6.3 | DBN (1,5-diazabicyclo[4.3.0]non-5-ene) | 1-methylpyrrolidone |
| Example A6.4 | ethanolamine | dimethylsulfoxide |
| Example A6.5 | ethanolamine | dimethylformamide |
| Example A6.6 | piperidine | dimethylacetamide |
| Example A6.7 | piperidine | 1-methylpyrrolidone |
| Example A6.8 | sodium methylate | dimethylsulfoxide |

The reaction end point is confirmed by thin layer chromatography or high performance liquid chromatography.

After the reaction, the product (106) is obtained from the reaction mixture through ordinary product isolation by liquid-liquid separation, column chromatography or crystallization by addition of a poor solvent to the reaction mixture.

The desired product (106) is obtained as a brownish oil which crystallizes in form of yellow crystals (0.24 g, 10%).

Melting point: 139.4-141.0° C.

Example A7

Preparation of Compound of Formula

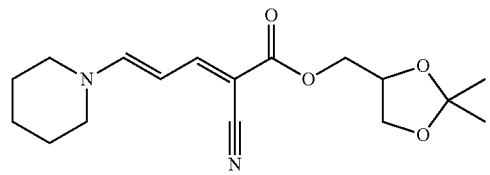

(107)

27.84 grams of piperidine are condensed with 1,1,3,3-tetramethoxypropane in acetic acid, concentrated and treated with 56.77 grams of (2,2-dimethyl-1,3-dioxolan-4-yl) methyl cyanoacetate in the presence of an organic base and a solvent.

The following base/solvent combinations are used:

| Example | Base | Solvent |
|---|---|---|
| Example A7.1 | DBU (1,8-diazabicyclo[5.4.0]undec-7-ene) | dimethylformamide |
| Example A7.2 | DBN (1,5-diazabicyclo[4.3.0]non-5-ene) | dimethylacetamide |
| Example A7.3 | DBN (1,5-diazabicyclo[4.3.0]non-5-ene) | 1-methylpyrrolidone |
| Example A7.4 | DBN (1,5-diazabicyclo[4.3.0]non-5-ene) | dimethylsulfoxide |
| Example A7.5 | DBU (1,8-diazabicyclo[5.4.0]undec-7-ene) | dimethylformamide |
| Example A7.6 | piperidine | dimethylacetamide |
| Example A7.7 | piperidine | 1-methylpyrrolidone |
| Example A7.8 | piperidine | dimethylsulfoxide |

74.74 grams of the compound (107) are obtained yielding yellow crystals.

Example A8

Preparation of Compound of Formula

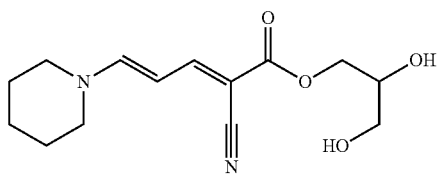

(108)

70 ml of hydro chloride acid (1 N) are added to a solution of 74.74 grams of merocyanine compound (107) in 350 ml of ethanol. The reaction mixture is stirred for 24 hours at 40° C. After adding water the product is extracted several times with ethyl acetate. The combined organic phases are dried with sodium sulphate, filtrated and concentrated under vacuum yielding the crude product as a brown oil.

After crystallization 34.44 grams of the product is yielded as a yellow powder.

Melting point: 101° C.

Example A9

Preparation of the Compound of Formula

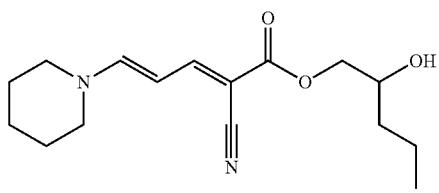

(109)

236.72 grams of piperidine are condensed with 1,1,3,3-tetramethoxypropane in acetic acid, concentrated and treated with 217.24 grams of 1-(2-hydroxy)pentyl cyanoacetate in the presence of an organic base and a solvent.

The following base/solvent combinations are used:

| Example | Base | Solvent |
|---|---|---|
| Example A9.1 | DBU (1,8-diazabicyclo[5.4.0]undec-7-ene) | dimethylformamide |
| Example A9.2 | DBU (1,8-diazabicyclo[5.4.0]undec-7-ene) | dimethylacetamide |
| Example A9.3 | piperidine | 1-methylpyrrolidone |
| Example A9.4 | piperidine | dimethylsulfoxide |
| Example A9.5 | DBU (1,8-diazabicyclo[5.4.0]undec-7-ene) | dimethylformamide |
| Example A9.6 | DBU (1,8-diazabicyclo[5.4.0]undec-7-ene) | dimethylacetamide |
| Example A9.7 | DBU (1,8-diazabicyclo[5.4.0]undec-7-ene) | 1-methylpyrrolidone |
| Example A9.8 | DBU (1,8-diazabicyclo[5.4.0]undec-7-ene) | dimethylsulfoxide |

500 grams of the crude product (109) are obtained yielding a dark brown oil.

After column chromatography (silica gel, eluent: toluene/ethyl acetate) and crystallization 53.09 grams (23%) of the desired product (109) are obtained yielding yellow crystals.

Melting point: 130° C.

Example A10

Preparation of Compound of Formula

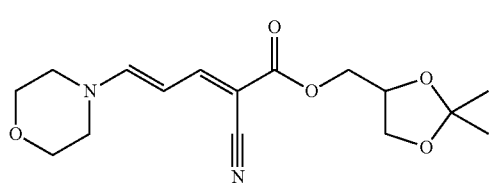

(110)

1.81 grams of morpholine are treated with 1,1,3,3-tetramethoxypropane in acetic acid, concentrated and treated with 1.89 grams of (2,2-dimethyl-1,3-dioxolan-4-yl)methyl cyanoacetate in the presence of an organic base and a solvent.

The following base/solvent combinations are used:

| Example | Base | Solvent |
|---|---|---|
| Example A10.1 | DBU (1,8-diazabicyclo[5.4.0]undec-7-ene) | dimethylformamide |
| Example A10.2 | DBU (1,8-diazabicyclo[5.4.0]undec-7-ene) | dimethylacetamide |
| Example A10.3 | DBN (1,5-diazabicyclo[4.3.0]non-5-ene) | 1-methylpyrrolidone |
| Example A10.4 | morpholine | dimethylsulfoxide |
| Example A10.5 | morpholine | dimethylformamide |
| Example A10.6 | morpholine | dimethylacetamide |
| Example A10.7 | sodium methylate | isopropanol |
| Example A10.8 | sodium methylate | dimethylsulfoxide |

2.99 grams of the crude product (110) are obtained yielding a dark brown oil. After column chromatography (silica gel, eluent: toluene/acetone) and crystallization 1.17 grams (50%) of the compound (110) are obtained yielding yellowish crystals.

Example A11

Preparation of the Compound of Formula

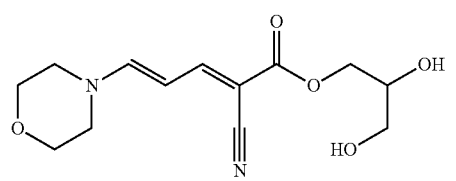

(111)

1 ml of hydro chloride acid (1 N) are added to a solution of 1.17 grams of merocyanine compound (110) in 5 ml of ethanol. The reaction mixture is stirred for 16 hours at room temperature.

The product is filtered off and washed with small amounts of ethanol and water.

After drying under vacuum 0.36 grams of the product (111) is yielded as a yellowish powder.

Melting point: 144.5-146.0° C.

Example A12

Preparation of the Compound of Formula

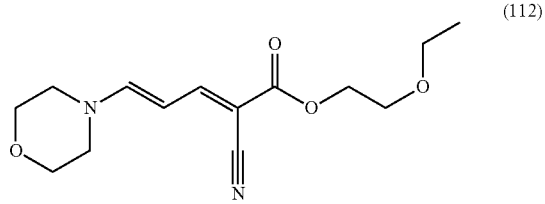 [SMILES: CCOCCOC(=O)/C(C#N)=C/C=C/N1CCOCC1]
(112)

83.40 grams of morpholine are condensed with 1,1,3,3-tetramethoxypropane in acetic acid and treated with 47.15 grams of 2-ethoxyethyl cyanoacetate in the presence of the organic base and a solvent.

The following base/solvent combinations are used:

| Example | Base | Solvent |
|---|---|---|
| Example A12.1 | DBU (1,8-diazabicyclo[5.4.0]undec-7-ene) | dimethylformamide |
| Example A12.2 | DBN (1,5-diazabicyclo[4.3.0]non-5-ene) | dimethylacetamide |
| Example A12.3 | DBN (1,5-diazabicyclo[4.3.0]non-5-ene) | 1-methylpyrrolidone |
| Example A12.4 | DBN (1,5-diazabicyclo[4.3.0]non-5-ene) | dimethylsulfoxide |
| Example A12.5 | DBU (1,8-diazabicyclo[5.4.0]undec-7-ene) | dimethylformamide |
| Example A12.6 | morpholine | dimethylacetamide |
| Example A12.7 | morpholine | 1-methylpyrrolidone |
| Example A12.8 | sodium methylate | dimethylsulfoxide |

32.58 grams of the compound (112) are obtained yielding yellow crystals.

Melting point: 81.5° C.

Example A13

Preparation of the Compound of Formula

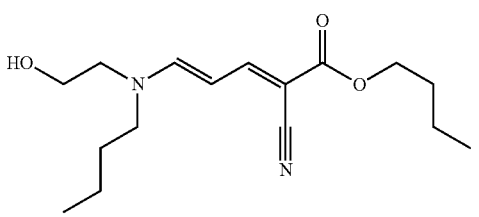
(113)

By using 113.00 grams of ethyl-2-hydroxyethylaminoacrolein and 102.47 grams of n-butyl cyanoacetate 123.46 grams of the crude product are obtained yielding a brown oil.

After crystallization 23.29 g of the product is obtained yielding yellowish crystals.

Melting point: 78.0° C.

Example A14

Preparation of the Compound of Formula

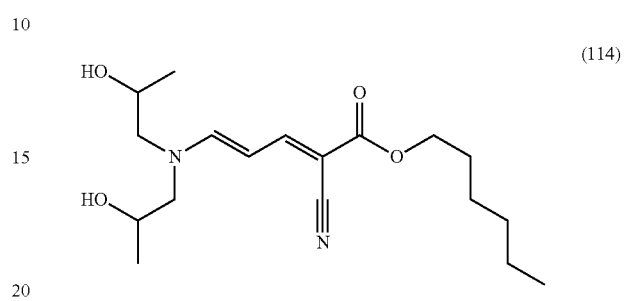
(114)

The merocyanine compound (114) is synthesized according to the synthesis of merocyanine (113) yielding the desired product as a brownish oil.

$^1$H-NMR (CDCl$_3$):

δ=7.73 (1H, d), 7.24 (1H, d), 5.5 (1H, t), 4.07-4.33 (5H, m), 3.44-3.55 (2H, m), 3.16-3.26 (2H, m), 1.67 (2H, m), 1.22-1.45 (12H, m), 0.9 (3H, m).

Example A15

Preparation of the Compound of Formula

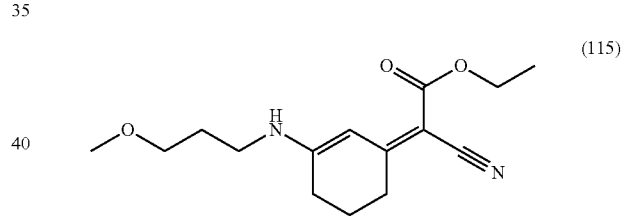
(115)

122.23 grams of 3-[(3-methoxypropyl)amino]-2-cyclohexen-1-one are alkylated with dimethylsulfate or alternatively with diethylsulfate and treated with 75.45 grams of ethyl cyanoacetate in approximately equimolar proportions in the presence of a base and optionally a solvent.

The following base/solvent combinations are used:

| Example | Base | Solvent |
|---|---|---|
| Example A15.1 | DBU (1,8-diazabicyclo[5.4.0]undec-7-ene) | dimethylacetamide |
| Example A15.2 | triethylamine | isopropanol |
| Example A15.3 | 3-methoxypropylamine | isopropanol |
| Example A15.4 | 3-methoxypropylamine | tert-amylalcohol |
| Example A15.5 | 3-methoxypropylamine | toluene |
| Example A15.6 | 3-methoxypropylamine | dimethylformamide |
| Example A15.7 | 3-methoxypropylamine | no solvent |
| Example A15.8 | N-morpholine | isopropanol |

Completion of the alkylation reaction can be monitored for example by TLC, GC or HPLC methods.

162.30 grams of the product (115) are obtained yielding a brown oil.

After crystallization the product is obtained yielding yellowish crystals.
Melting point: 92.7° C.

Example A16

Preparation of the Compound of Formula

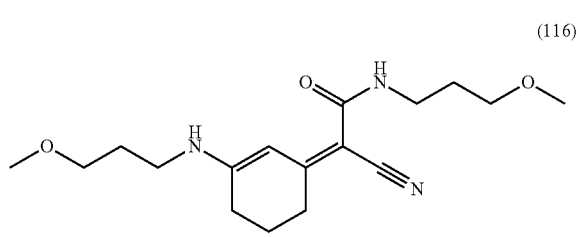

(116)

101.00 grams of 3-[(3-methoxypropyl)amino]-2-cyclohexen-1-one are alkylated with dimethylsulfate or alternative with diethylsulfate and treated with 86.00 grams of 2-cyano-N-(3-methoxy-propyl)-acetamide in approximately equimolar proportions in the presence of a base and optionally a solvent.

The following base/solvent combinations are used:

| Example | Base | Solvent |
| --- | --- | --- |
| Example A16.1 | DBU (1,8-diazabicyclo[5.4.0]undec-7-ene) | dimethylacetamide |
| Example A16.2 | triethylamine | isopropanol |
| Example A16.3 | 3-methoxypropylamine | isopropanol |
| Example A16.4 | 3-methoxypropylamine | tert-amyl alcohol |
| Example A16.5 | 3-methoxypropylamine | toluene |
| Example A16.6 | 3-methoxypropylamine | dimethylformamide |
| Example A16.7 | 3-methoxypropylamine | no solvent |

The crude product (116) is obtained yielding a dark brown oil.

After silica gel column chromatography (eluent: toluene/methanol 99:1) 81.8 grams of the product are obtained yielding yellowish crystals.
Melting point: 84.7-85.3° C.

Example A17

Preparation of the Compound of Formula

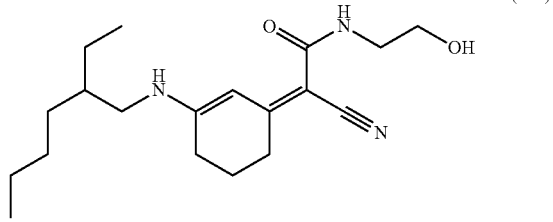

(117)

111.0 grams of 3-[(2-ethylhexyl)amino]-2-cyclohexen-1-one are alkylated with dimethylsulfate or alternatively with diethylsulfate and are then treated with 64.10 grams of 2-cyano-N-(2-hydroxy-ethyl)-acetamide in the presence of a base and optionally a solvent.

The following base/solvent combinations are used:

| Example. | Base | Solvent |
| --- | --- | --- |
| Example A17.1 | DBU (1,8-diazabicyclo[5.4.0]undec-7-ene) | dimethylacetamide |
| Example A17.2 | triethylamine | isopropanol |
| Example A17.3 | ethanolamine | isopropanol |
| Example A17.4 | 2-ethylhexylamine | tert-amyl alcohol |
| Example A17.5 | ethanolamine | toluene |
| Example A17.6 | ethanolamine | dimethylformamide |
| Example A17.7 | ethanolamine | no solvent |

The reaction temperature is between 60 to 120° C.
The crude product is obtained yielding brownish crystals.
After recrystallization 97 grams of the product were obtained yielding yellowish crystals.
Melting point: 117-119° C.

Example A18

Preparation of the Compound of Formula

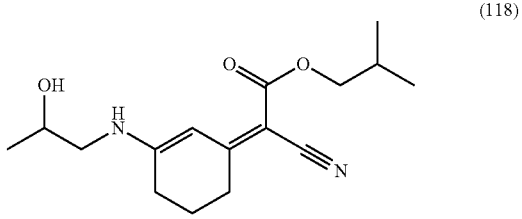 [SMILES: CC(C)COC(=O)/C(C#N)=C1\C=C(NCC(C)O)CCC1]

(118)

100.56 grams of 3-[(2-hydroxypropyl)amino]-2-cyclohexen-1-one are alkylated with dimethylsulfate or alternatively with diethylsulfate and treated with 84.70 grams of isobutyl cyanoacetate in the presence of a base and optionally a solvent.

The following base/solvent combinations are used:

| Example | Base | Solvent |
| --- | --- | --- |
| Example A18.1 | DBU (1,8-diazabicyclo[5.4.0]undec-7-ene) | dimethylacetamide |
| Example A18.2 | triethylamine | isopropanol |
| Example A18.3 | 1-amino-2-propanol | isopropanol |
| Example A18.4 | N-methylmorpholine | tert-amyl alcohol |
| Example A18.5 | 1-amino-2-propanol | toluene |
| Example A18.6 | 1-amino-2-propanol | dimethylformamide |
| Example A18.7 | 1-amino-2-propanol | no solvent |

15.97 grams of the crude product (118) is obtained yielding a dark brown oil.

After silica gel chromatography (eluent: hexane/ethyl acetate) 45.67 grams of the product (118) are obtained yielding yellowish crystals. Melting point: 106.7° C.

Example A19

Preparation of the Compound of Formula

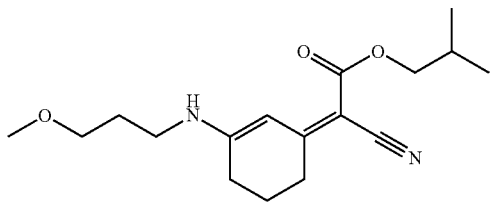

(119)

13.09 grams of 3-[(3-methoxypropyl)amino]-2-cyclohexen-1-one are alkylated with dimethylsulfate or alternatively with diethylsulfate and treated with 10.12 grams of isobutyl cyanoacetate in the presence of a base and optionally a solvent.

The following base/solvent combinations are used:

| Example | Base | Solvent |
| --- | --- | --- |
| Example A19.1 | DBU (1,8-diazabicyclo[5.4.0]undec-7-ene) | dimethylacetamide |
| Example A19.2 | triethylamine | isopropanol |
| Example A19.3 | 3-methoxypropylamine | isopropanol |
| Example A19.4 | N-methylmorpholine | tert-amyl alcohol |
| Example A19.5 | 3-methoxypropylamine | toluene |
| Example A19.6 | 3-methoxypropylamine | dimethylformamide |
| Example A19.7 | 3-methoxypropylamine | no solvent |

15.97 grams of the crude product (119) are obtained yielding a dark brown oil.

After silica gel chromatography (eluent: toluene/acetone) 13.46 grams of the product (119) are obtained yielding yellowish crystals. Melting point: 96.3° C.

Example A20

Preparation of the Compound of Formula

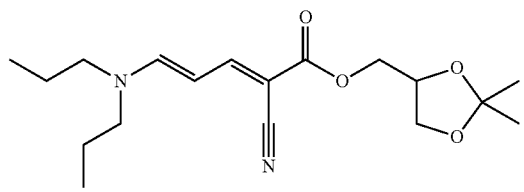

(120)

222.62 grams of dipropylamine are condensed with 1,1,3,3-tetramethoxypropane in acetic acid and treated with 200.13 grams of (2,2-dimethyl-1,3-dioxolan-4-yl)methyl cyanoacetate in the presence of an organic base and a solvent as described on page 4 in US2003/0181483A1.

The following Base/solvent combinations are used:

| Example | Base | Solvent |
| --- | --- | --- |
| Example A20.1 | DBU (1,8-diazabicyclo[5.4.0]undec-7-ene) | dimethylformamide |
| Example A20.2 | DBN (1,5-diazabicyclo[4.3.0]non-5-ene) | dimethylacetamide |
| Example A20.3 | DBN (1,5-diazabicyclo[4.3.0]non-5-ene) | 1-methylpyrrolidone |
| Example A20.4 | DBN (1,5-diazabicyclo[4.3.0]non-5-ene) | dimethylsulfoxide |
| Example A20.5 | DBU (1,8-diazabicyclo[5.4.0]undec-7-ene) | dimethylformamide |
| Example A20.6 | dipropylamine | dimethylacetamide |
| Example A20.7 | sodium methylate | 1,2-dimethoxyethane |
| Example A20.8 | N-methylmorpholine | dimethylsulfoxide |

327 grams of the crude product (120) are obtained yielding a brown oil.

Example A21

Preparation of the Compound of Formula

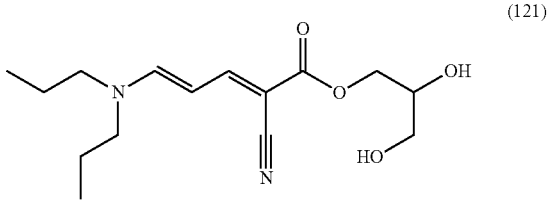 [SMILES: CCCN(/C=C/C=C(\C#N)C(=O)OCC(O)CO)CCC]

(121)

317 ml of hydro chloride acid (1 N) are added to a solution of 327 grams of crude merocyanine (120) in 990 ml of ethanol.

The reaction mixture is stirred for 16 hours at room temperature.

After removal of ethanol in vacuum the reaction mass was taken up in water and the product is extracted several times with ethyl acetate.

The collected organic phases are concentrated in vacuum.

After silica gel column chromatography (eluent: toluene/ethyl acetate) and crystallization 70 grams of the desired product (121) are obtained yielding yellowish crystals.

Melting point: 73° C.

Example A22

Preparation of the Compound of Formula

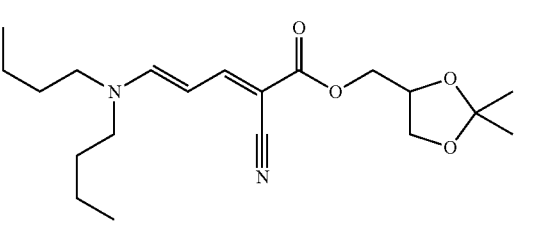

(122)

66.43 grams of dibutylamine are condensed with 1,1,3,3-tetramethoxypropane in acetic acid and treated with 46.81 grams of (2,2-dimethyl-1,3-dioxolan-4-yl)methyl cyanoacetate in the presence of an organic base and a solvent.

The following Base/solvent combinations are used:

| Example | Base | Solvent |
| --- | --- | --- |
| Example A22.1 | DBU (1,8-diazabicyclo[5.4.0]undec-7-ene) | dimethylformamide |
| Example A22.2 | DBN (1,5-diazabicyclo[4.3.0]non-5-ene) | dimethylacetamide |
| Example A22.3 | DBN (1,5-diazabicyclo[4.3.0]non-5-ene) | 1-methylpyrrolidone |
| Example A22.4 | DBN (1,5-diazabicyclo[4.3.0]non-5-ene) | dimethylsulfoxide |
| Example A22.5 | DBU (1,8-diazabicyclo[5.4.0]undec-7-ene) | dimethylformamide |
| Example A22.6 | dibutylamine | dimethylacetamide |
| Example A22.7 | N-methylmorpholine | 1-methylpyrrolidone |
| Example A22.8 | sodium methylate | dimethylsulfoxide |

82.49 grams of the crude product (122) are obtained yielding a black oil.

Example A23

Preparation of the Compound of Formula

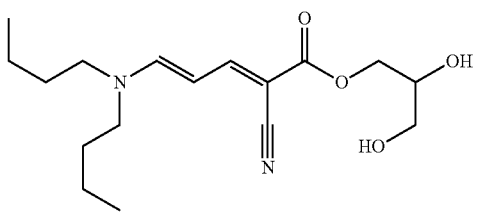

(123)

80 ml of hydro chloride acid (1 N) are added to a solution of 82.5 grams of crude merocyanine (122) in 250 ml of ethanol. The reaction mixture is stirred for 16 hours at room temperature.

After removal of ethanol in vacuum the reaction mass is taken up in water and the product (122) is extracted several times with ethyl acetate.

The collected organic phases are concentrated in vacuum.

After silica gel column chromatography (eluent: toluene/acetone) 37.85 grams of the desired product are obtained yielding a brownish oil.

HPLC (210 nm): 99.3 A-%. $^1$H-NMR (CDCl$_3$): δ=7.8 (1H, d), 7.2 (1H, d), 5.6 (1H, t), 4.27 (2H, m), 3.98 (1H, m), 3.5-3.7 (2H, m), 3.25-3.33 (4H, m), 3.00 (2H, s), 1.61 (4H, m), 1.35 (4H, m), 0.96 (6H, m).

Example A24

Preparation of the Compound of Formula

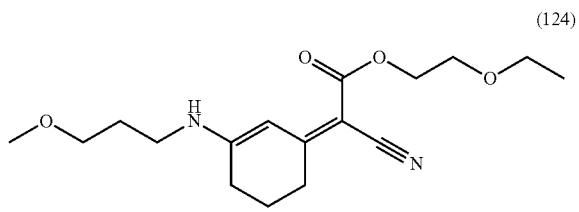 [SMILES: CCOCCOC(=O)/C(C#N)=C1\C=C(NCCCOC)CCC1]

(124)

148.4 grams of 3-[(3-methoxypropyl)amino]-2-cyclohexen-1-one are alkylated with dimethylsulfate or alternatively with diethylsulfate and treated with 130.00 grams of 2-ethoxyethyl cyanoacetate in the presence of an organic base and a solvent.

The following base/solvent combinations are used:

| Example | Base | Solvent |
| --- | --- | --- |
| Example A24.1 | DBU (1,8-diazabicyclo[5.4.0]undec-7-ene) | dimethylacetamide |
| Example A24.2 | triethylamine | isopropanol |
| Example A24.3 | 3-methoxypropylamine | isopropanol |
| Example A24.4 | N-methylmorpholine | tert-amyl alcohol |
| Example A24.5 | 3-methoxypropylamine | toluene |
| Example A24.6 | 3-methoxypropylamine | dimethylformamide |
| Example A24.7 | 3-methoxypropylamine | no solvent |

After column chromatography (silica gel, eluent: toluene/ethyl acetate) and crystallization 134.96 grams of the desired product (124) are obtained yielding yellow crystals.

Melting point: 90-91.5° C.

UV Shielding Properties

The UV shielding properties of the merocyanine derivatives are investigated by measuring their UV spectra in ethanol. In the following table the investigated absorption maxima ($\lambda_{max}$) together with the corresponding $A^{1\%}_{1cm}$ values are listed.

| Comp. No. | Absorption maximum | |
| --- | --- | --- |
| | $\lambda_{max}$ | $A^{1\%}_{1\,cm}$ |
| (101) | 380 | 2283 |
| (102) | 380 | 2046 |
| (103) | 380 | 1965 |
| (104) | 381 | 2568 |
| (105) | 381 | 2252 |
| (106) | 380 | 2530 |
| (108) | 381 | 2467 |
| (111) | 380 | 2414 |
| (113) | 381 | 2235 |
| (115) | 385 | 2207 |
| (116) | 385 | 1644 |
| (117) | 386 | 1618 |
| (118) | 385 | 2083 |
| (119) | 385 | 2036 |
| (121) | 381 | 2230 |
| (124) | 385 | 1947 |

All merocyanine compounds according to the present invention possess extraordinary high shielding properties in the UV region as indicated by $A^{1\%}_{1cm}$ values above 1500.

The invention claimed is:
1. A compound of formula

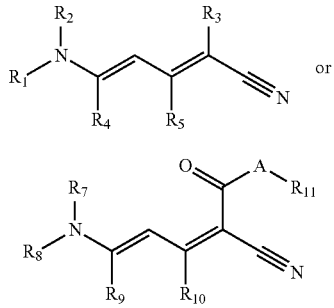

and/or its E/E-, E/Z- or Z/Z geometrical isomer forms; wherein
$R_1$ and $R_2$ independently of each other are hydrogen; $C_4$-$C_{12}$alkyl; or hydroxyl-$C_3$-$C_{12}$alkyl;
$R_3$ is a —(C=O)O$R_6$ group; or a —(CO)NH$R_6$ group;
$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;
$R_4$ and $R_5$ are hydrogen; or $R_4$ and $R_5$ form a —(CH$_2$)$_n$— ring which is optionally interrupted by one or more than one —O— or by —NH—;
n is a number from 2 to 7;
$R_7$ and $R_8$ independently of each other are hydrogen; $C_1$-$C_{22}$alkyl, $C_2$-$C_{22}$alkenyl, $C_2$-$C_{22}$alkinyl, which is interrupted by one or more than one O or substituted by one or more than one OH, $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—;
or $R_7$ and $R_8$ together with the nitrogen atom linking them form a —(CH$_2$)$_n$— ring which is optionally interrupted by one or more than one —O—;
$R_9$ and $R_{10}$ are hydrogen; or $R_9$ and $R_{10}$ form a —(CH$_2$)$_n$— ring which is optionally interrupted by —O— or by —NH—;
A is —O—; or —NH;
$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O; or $C_1$-$C_{22}$alkyl or $C_2$-$C_{22}$alkenyl which is substituted by $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—;
with the proviso that
(I) at least one of $R_1$, $R_2$, and $R_6$ is substituted by hydroxyl;
(II) if one of $R_1$ is hydroxyethyl, $R_2$ is not hydrogen, methyl or ethyl or hydroxyethyl; and if $R_1$ is hydrogen, $R_2$ is not 1-hydroxy-3-methyl-but-2-yl;
(III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical; and
(IV) at least one of $R_7$ and $R_8$, or $R_{11}$ is interrupted by one or more than one —O—.
2. The compound according to claim 1, wherein
$R_1$ and $R_2$ independently of each other are hydrogen; $C_4$-$C_{12}$alkyl; or hydroxyl-$C_3$-$C_{12}$alkyl;
$R_3$ is a —(C=O)O$R_6$ group; or a —(CO)NH$R_6$ group;
$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;
$R_4$ and $R_5$ are hydrogen; or $R_4$ and $R_5$ form a —(CH$_2$)$_n$— ring which is optionally interrupted by —O— or by —NH—;
n is a number from 2 to 7;
$R_7$ and $R_8$ independently of each other are hydrogen; $C_1$-$C_{22}$alkyl, $C_2$-$C_{22}$alkenyl, $C_2$-$C_{22}$alkinyl, which is interrupted by one or more than one O or substituted by one or more than one OH; or $R_7$ and $R_8$ together with the nitrogen atom linking them form a —(CH$_2$)$_n$— ring which is optionally interrupted by one or more than one —O—;
$R_9$ and $R_{10}$ are hydrogen; or $R_9$ and $R_{10}$ form a —(CH$_2$)$_n$— ring which is optionally interrupted by —O— or by —NH—;
A is —O—; or —NH;
$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O;
with the proviso that
(I) at least one of $R_1$, $R_2$, and $R_6$ is substituted by hydroxyl;
(II) if one of $R_1$ is hydroxyethyl, $R_2$ is not hydrogen, methyl or ethyl or hydroxyethyl; and if $R_1$ is hydrogen, $R_2$ is not 1-hydroxy-3-methyl-but-2-yl;
(III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical; and
(IV) at least one of $R_7$ and $R_8$, or $R_1$ is interrupted by one or more than one —O—.
3. A compound which corresponds to one of the following formulas

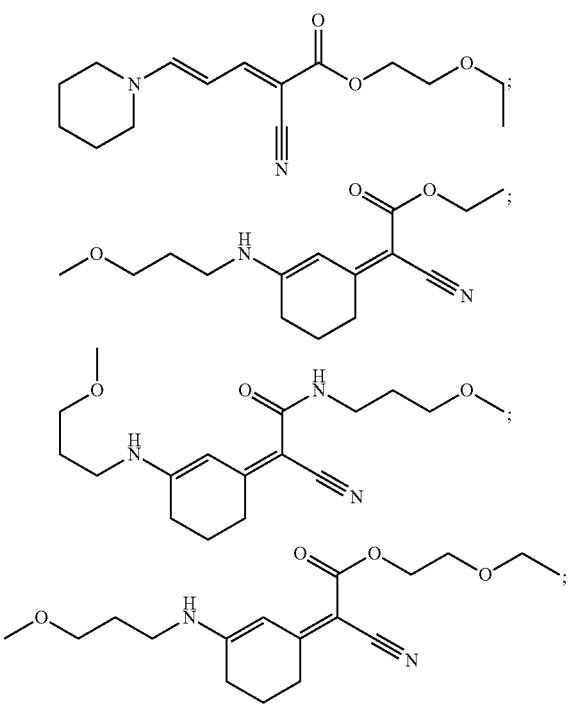

-continued

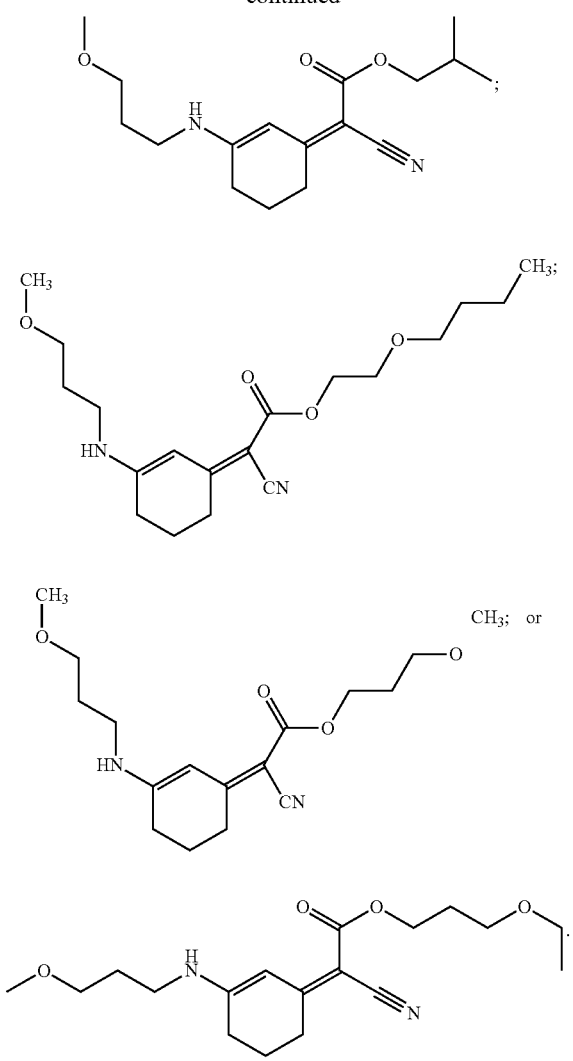

4. A compound which is 2-ethoxyethyl(2Z)-cyano{3-[(3-methoxypropyl)amino]cyclohex-2-en-1-ylidene}ethanoate in its E/Z geometrical isomer corresponding to the formula

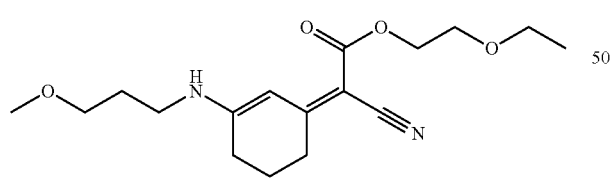

and/or its E/E geometrical form of formula

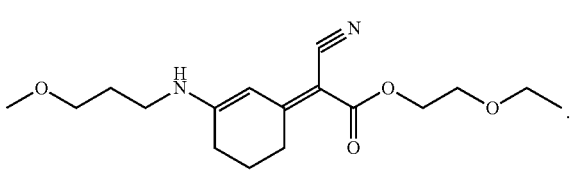 [SMILES: CCOCCOC(=O)/C(C#N)=C1/C=C(NCCCOC)CCC1]

5. A compound of formula

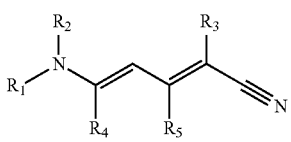
(1)

and/or its E/E-, E/Z- or Z/Z geometrical isomer forms; wherein $R_1$ and $R_2$ independently of each other are hydrogen; $C_1$-$C_{22}$alkyl, $C_2$-$C_{22}$alkenyl, $C_2$-$C_{22}$alkinyl, which are optionally substituted by at least one hydroxyl; or $R_1$ and $R_2$ together with the nitrogen atom linking them form a —$(CH_2)_n$— ring which is optionally interrupted by —O— or by —NH—;

$R_3$ is a —(C=O)O$R_6$ group; or a —(CO)NH$R_6$ group;

$R_6$ is $C_1$-$C_{12}$alkyl, which is optionally substituted by one or more than one hydroxyl;

$R_4$ and $R_5$ are hydrogen; or $R_4$ and $R_5$ form a —$(CH_2)_n$— ring which is optionally interrupted by one or more than one —O— or by —NH—;

n is a number from 2 to 7;

with the proviso that (I) at least one of $R_1$, $R_2$, and $R_6$ is substituted by hydroxyl;

(II) if one of $R_1$ is hydroxyethyl, $R_2$ is not hydrogen, methyl or ethyl or hydroxyethyl; and if $R_1$ is hydrogen, $R_2$ is not 1-hydroxy-3-methyl-but-2-yl; and (III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical.

6. The compound of formula (1) according to claim 5, wherein one of $R_1$ and $R_2$ is $C_4$-$C_{22}$alkyl; or $R_1$ and $R_2$ together with the nitrogen atom linking them form a —$(CH_2)_n$-ring which is optionally interrupted by —O— and/or —NH—.

7. A compound of formula

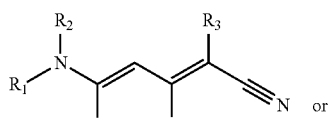
(1)
or
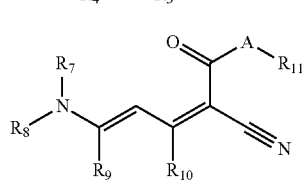
(2)

and/or its E/E-, E/Z- or Z/Z geometrical isomer forms; wherein $R_1$ and $R_2$ respectively together with the linking nitrogen atom to form a piperidyl, radical, or a morpholinyl radical;

$R_3$ is a —(C=O)O$R_6$ group; or a —(CO)NH$R_6$ group;

$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;

$R_4$ and $R_5$ are hydrogen; or $R_4$ and $R_5$ form a —$(CH_2)_n$— ring which is optionally interrupted by one or more than one —O— or by —NH—;

n is a number from 2 to 7;

$R_7$ and $R_8$ respectively together with the linking nitrogen atom form a piperidyl radical or a morpholinyl radical;

$R_9$ and $R_{10}$ are hydrogen; or $R_9$ and $R_{10}$ form a —$(CH_2)_n$— ring which is optionally interrupted by —O— or by —NH—;

A is —O—; or —NH;

$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O; or $C_1$-$C_{22}$alkyl or $C_2$-$C_{22}$alkenyl which is substituted by $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—;

with the proviso that (I) at least one of $R_1$, $R_2$, and $R_6$ is substituted by hydroxyl;

(II) if one of $R_1$ is hydroxyethyl, $R_2$ is not hydrogen, methyl or ethyl or hydroxyethyl; and if $R_1$ is hydrogen, $R_2$ is not 1-hydroxy-3-methyl-but-2-yl;

(III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical; and (IV) at least one of $R_7$ and $R_8$, or $R_{11}$ is interrupted by one or more than one —O—.

8. A compound of formula

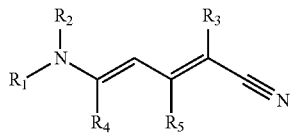

(1)

and/or its E/E-, E/Z- or Z/Z geometrical isomer forms; wherein $R_1$ and $R_2$ independently of each other are hydrogen or $C_1$-$C_{22}$alkyl; or hydroxyl-$C_1$-$C_{22}$alkyl; or $R_1$ and $R_2$ together with the nitrogen atom are linked together to form a piperidyl or morpholinyl radical;

$R_3$ is a —(C=O)O$R_6$ group; or a —(CO)NH$R_6$ group;

$R_6$ is $C_1$-$C_{22}$alkyl, which may be substituted by one or more than one —OH;

$R_4$ and $R_5$ are hydrogen; or $R_4$ and $R_5$ are linked together to form a carbocyclic ring which contains 6 carbon atoms;

n is a number from 2 to 7;

with the proviso that (I) at least one of $R_1$, $R_2$, and $R_6$ is substituted by hydroxyl;

(II) if one of $R_1$ is hydroxyethyl, $R_2$ is not hydrogen, methyl or ethyl or hydroxyethyl; and if $R_1$ is hydrogen, $R_2$ is not 1-hydroxy-3-methyl-but-2-yl; and (III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical.

9. The compound of formula (1) according to claim 8, wherein $R_1$ and $R_2$ independently of each other are hydrogen; or hydroxyl-$C_1$-$C_{22}$alkyl;

wherein at least one of $R_1$ and $R_2$ is hydroxyl-$C_1$-$C_{22}$alkyl;

$R_3$ is a —(C=O)O$R_6$ group; or a —(C=O)NH$R_6$ group;

$R_6$ is $C_1$-$C_{22}$alkyl; and $R_4$ and $R_5$ are hydrogen; or $R_4$ and $R_5$ are linked together to form a carbocyclic ring which contains 6 carbon atoms.

10. A compound of formula

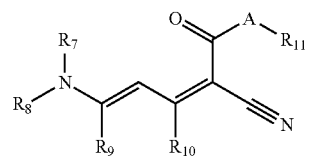

and/or its E/E-, E/Z- or Z/Z geometrical isomer forms; wherein $R_7$ and $R_8$ independently of each other are hydrogen; $C_1$-$C_{22}$alkyl, $C_2$-$C_{22}$alkenyl, $C_2$-$C_{22}$alkinyl, which is interrupted by one or more than one O or substituted by one or more than one OH, $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—;

or $R_7$ and $R_8$ together with the nitrogen atom form a morpholinyl or piperidyl radical;

$R_9$ and $R_{10}$ are hydrogen; or $R_9$ and $R_{10}$ are linked together to form a carbocyclic ring which contains 6 carbon atoms;

A is —O—; or —NH;

$R_{11}$ is $C_1$-$C_{22}$alkyl, which is optionally interrupted by one or more than one O;

with the proviso that at least one of $R_7$ and $R_8$, or $R_{11}$ is interrupted by one or more than one —O—.

* * * * *

UNITED STATES PATENT AND TRADEMARK OFFICE
CERTIFICATE OF CORRECTION

PATENT NO.        : 9,550,730 B2
APPLICATION NO.   : 14/232915
DATED             : January 24, 2017
INVENTOR(S)       : Barbara Winkler et al.

It is certified that error appears in the above-identified patent and that said Letters Patent is hereby corrected as shown below:

On the Title Page

At item (75), Line 1, "Lorrach" should be -- Lörrach --.

At item (75), Line 6, "ILona" should be -- Ilona --.

In the Claims

At Column 46, Line 34, "$R_1$" should be -- $R_{11}$ --.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*